US012758603B2

(12) United States Patent
Swisa et al.

(10) Patent No.: US 12,758,603 B2
(45) Date of Patent: Oct. 13, 2026

(54) CANNABIDIOLIC ACID (CBDA) DERIVATIVES AND USES THEREOF

(71) Applicant: YISSUM RESEARCH DEVELOPMENT COMPANY OF THE HEBREW UNIVERSITY OF JERUSALEM LTD., Jerusalem (IL)

(72) Inventors: Reshef Swisa, Santa Monica, CA (US); Anat Iosub-Amir, Jerusalem (IL); Ron Shaharabani, Herzliya (IL); Raphael Mechoulam, Jerusalem (IL); Natalya M. Kogan, Kfar Adummim (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 629 days.

(21) Appl. No.: 18/000,224

(22) PCT Filed: Jun. 3, 2021

(86) PCT No.: PCT/IL2021/050661

§ 371 (c)(1),
(2) Date: Nov. 29, 2022

(87) PCT Pub. No.: WO2021/245671

PCT Pub. Date: Dec. 9, 2021

(65) Prior Publication Data

US 2023/0192588 A1 Jun. 22, 2023

Related U.S. Application Data

(60) Provisional application No. 63/033,847, filed on Jun. 3, 2020.

(51) Int. Cl.

| | |
|---|---|
| ***A61K 36/185*** | (2006.01) |
| ***A61K 31/05*** | (2006.01) |
| ***A61K 31/192*** | (2006.01) |
| ***A61K 31/352*** | (2006.01) |
| ***A61P 25/04*** | (2006.01) |
| ***A61P 25/08*** | (2006.01) |
| ***A61P 29/00*** | (2006.01) |
| ***C07C 63/64*** | (2006.01) |

(52) U.S. Cl.

CPC .......... *A61K 36/3482* (2024.05); *A61K 31/05* (2013.01); *A61K 31/192* (2013.01); *A61K 31/352* (2013.01); *A61P 25/04* (2018.01); *A61P 25/08* (2018.01); *A61P 29/00* (2018.01); *C07C 63/64* (2013.01)

(58) Field of Classification Search

CPC ..... A61K 31/05; A61K 31/192; A61K 31/352
See application file for complete search history.

(56) References Cited

U.S. PATENT DOCUMENTS

| | | | |
|---|---|---|---|
| 5,338,753 | A | 8/1994 | Burstein |
| 6,403,126 | B1 | 6/2002 | Webster |

FOREIGN PATENT DOCUMENTS

| | | | |
|---|---|---|---|
| CN | 111848365 | A | 10/2020 |
| CN | 112898190 | A | 6/2021 |
| WO | 9953917 | A1 | 10/1999 |
| WO | 2018091551 | A1 | 5/2018 |
| WO | 2018235079 | A1 | 12/2018 |
| WO | 2019079677 | A1 | 4/2019 |
| WO | 2020024009 | A1 | 2/2020 |
| WO | 2020031179 | A1 | 2/2020 |
| WO | 2020232545 | A1 | 11/2020 |
| WO | 2021007661 | A1 | 1/2021 |
| WO | 2021046640 | A1 | 3/2021 |

OTHER PUBLICATIONS

Appendino et al., (2008) Antibacterial cannabinoids from Cannabis sativa: a structure-activity study. J Nat Prod 71(8): 1427-1430.
Björkman (1982) Gas chromatography of cannabis constituents, including cannabinoid acids, with on-column alkylation and esterification. Journal of Chromatography A 237(3): 389-397.
Citti et al., (2018) Analysis of cannabinoids in commercial hemp seed oil and decarboxylation kinetics studies of cannabidiolic acid (CBDA). J Pharm Biomed Anal 149: 532-540.
Dhir (2018) Cannabidiol in Refractory Epilepsy. Studies in Natural Products Chemistry 58: 419-438.
Grlic (1962) A comparative study on some chemical and biological characteristics of various samples of cannabis resin. Bulletin on Narcotics 14(3): 37-46. 18 pages.
Hen-Shoval et al., (2018) Acute oral cannabidiolic acid methyl ester reduces depression-like behavior in two genetic animal models of depression. Behav Brain Res 351: 1-3.
Kabelik, Krejci and Santavy (1960) Hemp as a Medicament: Summary of the Study. Bulletin on Narcotics Issue 3-002. 1955—Acta Universitatis Palackianae Olomucensis—TOM. VI. 11 pages.
Mechoulam and Ben-Zvi (1969) Carboxylation of resorcinols with methylmagnesium carbonate. Synthesis of cannabinoid acids. J Chem Soc D pp. 343-344.
Mechoulam and Gaoni (1965) Hashish—IV: The isolation and structure of cannabinolic cannabidiolic and cannabigerolic acids. Tetrahedron 21(5): 1223-1229.
Obay et al., (2007) Antiepileptic effects of ghrelin on pentylenetetrazole-induced seizures in rats. Peptides 28(6): 1214-1219.
Pertwee et al., (2018) Cannabidiolic acid methyl ester, a stable synthetic analogue of cannabidiolic acid, can produce 5-HT1A receptor-mediated suppression of nausea and anxiety in rats. Br J Pharmacol 175(1): 100-112.
Potter et al., (2008) Potency of delta 9-THC and other cannabinoids in cannabis in England in 2005: implications for psychoactivity and pharmacology. J Forensic Sci 53(1): 90-94.
Schubert et al., (2019) Efficacy of Cannabinoids in a Pre-Clinical Drug-Screening Platform for Alzheimer's Disease. Mol Neurobiol 56(11): 7719-7730.

(Continued)

*Primary Examiner* — Sahar Javanmard
(74) *Attorney, Agent, or Firm* — Ballard Spahr LLP

(57) ABSTRACT

The present invention provides novel compounds comprising cannabidiolic acid (CBDA) derivatives, including acids and esters, and uses thereof in the treatment of various diseases, disorders, conditions and symptoms.

12 Claims, 6 Drawing Sheets

(56) References Cited

OTHER PUBLICATIONS

Takeda et al., (2009) Cannabidiol-2',6'-dimethyl ether, a cannabidiol derivative, is a highly potent and selective 15-lipoxygenase inhibitor. Drug Metab Dispos 37(8): 1733-1737.

Signal 3: DAD1 C, Sig=220, 5 Ref=off

| Peak # | RetTime [min] | Type | Width [min] | Area [mAU*s] | Height [mAU] | Area % |
|---|---|---|---|---|---|---|
| 1 | 5.181 | BB | 0.0566 | 9861.99316 | 2707.65137 | 99.8810 |
| 2 | 5.408 | BB | 0.0445 | 11.75308 | 4.21428 | 0.1190 |

CANNABIDIOLIC ACID (CBDA) DERIVATIVES AND USES THEREOF

FIELD OF THE INVENTION

The present invention relates to cannabidiolic acid (CBDA) derivatives, including acids and esters, and uses thereof in the treatment of various diseases, disorders, conditions and symptoms.

BACKGROUND OF THE INVENTION

Cannabidiol (CBD) is the major non-psychotropic phytocannabinoid compound in the plant *Cannabis sativa,* making up to 40% of the cannabinoids in Cannabis extracts (Grlic, Bull. Narc., 1976, 14:37-46). CBD is considered a lead compound for treating and preventing inflammatory and oxidative damage, see for example WO1999/053917.

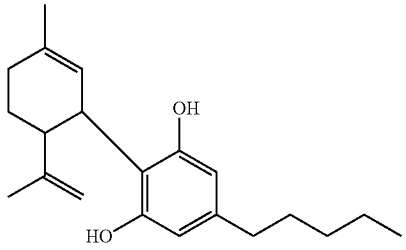

CBD

Cannabidiolic acid (CBDA) is also a major constituent of the *Cannabis sativa* plant and was first isolated in 1955 (Krejčí and Šantavý, 1955, Acta Univ Palacki Olomuc 6:59-66). Its structure was elucidated in 1965 by analysis of the physical properties of its methyl ester, cannabidiolic acid methyl ester (CBDA-ME) (Mechoulam and Gaoni, Tetrahedron, 1965, 21:1223-1229). Its synthesis from cannabidiol was subsequently reported (Mechoulam and Ben-Zvi, J. Chem. Soc. Commun., 1969, 7:343-344).

The cannabinoid acids are precursors of the natural cannabinoids (Potter et al., J. Forensic Sci., 2008, 53:90-94), potentially lowering the amount of drug required to induce effects. The decarboxylation of CBDA into CBD is enhanced by heat, indicating the relative instability of CBDA, thus lowering its potential to serve as a medication (Mechoulam, Academic Press, New York, 1973, 1-99; Citti et al., J. Pharm. Biomed. Anal., 2018, 16:532-540). Thus, CBDA-ME is a relatively unknown cannabinoid and remains understudied and its effects are only just starting to become clear.

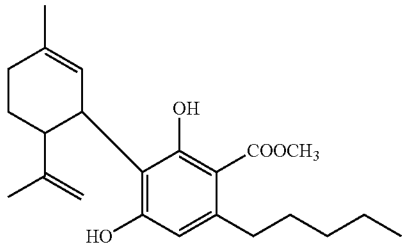

CBDA-ME

CBDA-ME is a stable derivative of CBDA and can be pharmacological active in vivo. Pertwee et al. (Brit. J. Pharmacology, 2018, 175:100-112) reported that the methyl ester of CBDA, designated HU-580 (also denoted herein EPM-301), displays a greater potency than CBDA in suppressing signs of both acute and anticipatory nausea, and of stress-induced anxiety in rats, and that it produces these effects in a 5-$HT_{1A}$ receptor-dependent manner. Another recent study (Hen-Shoval et al., Behav. Brain Res., 2018, 351:1-3) provides support for a potent anti-depressant effect after oral ingestion of a low dose (1 mg/kg) of HU-580 in two rat models.

WO 2018/235079 discloses compositions comprising CBDA esters and uses thereof in the treatment of a condition, disease or symptom associated with 5-$HT_{1A}$ receptors.

There is still an unmet medical need for effective therapies for use of non-psychoactive cannabinoids, particularly derivatives of CBD with improved properties and decreased potential for detrimental activity. These derivatives will be advantageous in the treatment of various diseases, conditions, disorders and symptoms, such as pain, impaired neurological functions including depression and anxiety, and inflammation.

SUMMARY OF THE INVENTION

The present invention provides novel compounds comprising cannabidiolic acid (CBDA) derivatives, including acid and esters, and uses thereof. The present invention further provides pharmaceutical compositions comprising CBDA derivatives, alone or in combination with one or more additional cannabinoid compounds, for use in treating various diseases and disorders and symptoms, including but not limited to pain, impaired neurological function, inflammation including respiratory inflammation, inflammatory bowel disease and autoimmune diseases, nausea, vomiting, convulsions, low appetite and glaucoma.

It is now disclosed, unexpectedly, that compositions comprising cannabidiolic acid (CBDA) or CBDA ester derivatives exhibit prolonged and significant therapeutic effects compared to cannabidiol (CBD). Advantageously, the pharmaceutical compositions disclosed herein are non-psychoactive. According to some embodiments the present invention provides pharmaceutical compositions comprising CBDA derivatives having superior pharmacokinetics compared to the commercially available cannabidiol (CBD).

According to one aspect, the present invention provides a compound represented by the structure of Formula (Ia), Formula (Ia)

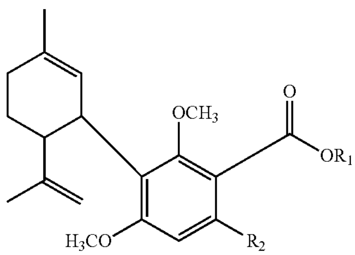

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, the compound is represented by the structure of Formula (Ib), Formula (Ib)

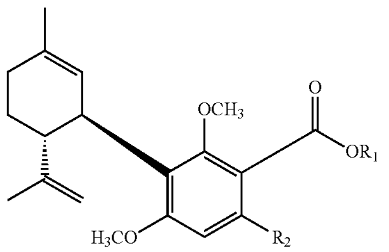

wherein $R_1$ and $R_2$ are defined as for Formula (Ia); and salts thereof.

According to some embodiments, the compound is represented by the structure of Formula (Ic), Formula (Ic)

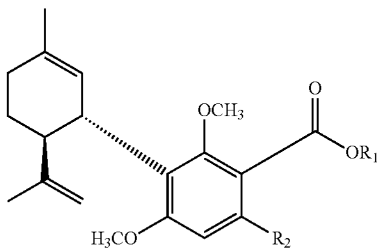

wherein $R_1$ and $R_2$ are defined as for Formula (Ia); and salts thereof.

According to some embodiments, the compound is represented by the structure of Formula (Id), Formula (Id)

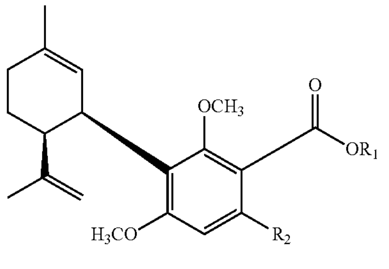

wherein $R_1$ and $R_2$ are defined as for Formula (Ia); and salts thereof.

According to some embodiments, the compound is represented by the structure of Formula (Ie), Formula (Ie)

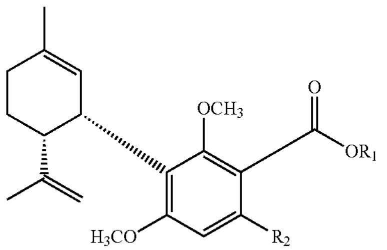

wherein $R_1$ and $R_2$ are defined as for Formula (Ia); and salts thereof.

According to some embodiments, $R_1$ is hydrogen. According to some embodiments, $R_1$ is a linear unsubstituted $C_1$-$C_{15}$ alkyl. According to some embodiments, $R_1$ is a linear substituted $C_1$-$C_{15}$ alkyl. According to some embodiments, $R_1$ is a branched unsubstituted $C_1$-$C_{15}$ alkyl. According to some embodiments, $R_1$ is a branched substituted $C_1$-$C_{15}$ alkyl. According to some embodiments, $R_1$ is methyl. According to some embodiments, $R_1$ is a linear unsubstituted $C_2$-$C_{15}$ alkenyl. According to some embodiments, $R_1$ is a linear substituted $C_2$-$C_{15}$ alkenyl. According to some embodiments, $R_1$ is a branched unsubstituted $C_2$-$C_{15}$ alkenyl. According to some embodiments, $R_1$ is a branched substituted $C_2$-$C_{15}$ alkenyl. According to some embodiments, $R_1$ is a linear unsubstituted $C_2$-$C_{15}$ alkynyl. According to some embodiments, $R_1$ is a linear substituted $C_2$-$C_{15}$ alkynyl. According to some embodiments, $R_1$ is a branched unsubstituted $C_2$-$C_{15}$ alkynyl. According to some embodiments, $R_1$ is a branched substituted $C_2$-$C_{15}$ alkynyl.

According to some embodiments, $R_2$ is a linear unsubstituted $C_1$-$C_{15}$ alkyl. According to some embodiments, $R_2$ is a linear substituted $C_1$-$C_{15}$ alkyl. According to some embodiments, $R_2$ is a branched unsubstituted $C_1$-$C_{15}$ alkyl. According to some embodiments, $R_2$ is a branched substituted $C_1$-$C_{15}$ alkyl. According to some embodiments, $R_2$ is a linear unsubstituted $C_5$ alkyl. According to some embodiments, $R_2$ is a linear unsubstituted $C_2$-$C_{15}$ alkenyl. According to some embodiments, $R_2$ is a linear substituted $C_2$-$C_{15}$ alkenyl. According to some embodiments, $R_2$ is a branched unsubstituted $C_2$-$C_{15}$ alkenyl. According to some embodiments, $R_2$ is a branched substituted $C_2$-$C_{15}$ alkenyl. According to some embodiments, $R_2$ is a linear unsubstituted $C_2$-$C_{15}$ alkynyl. According to some embodiments, $R_2$ is a linear substituted $C_2$-$C_{15}$ alkynyl. According to some embodiments, $R_2$ is a branched unsubstituted $C_2$-$C_{15}$ alkynyl. According to some embodiments, $R_2$ is a branched substituted $C_2$-$C_{15}$ alkynyl.

According to some embodiments, the compound is represented by the structure of Formula (IIa), Formula (IIa)

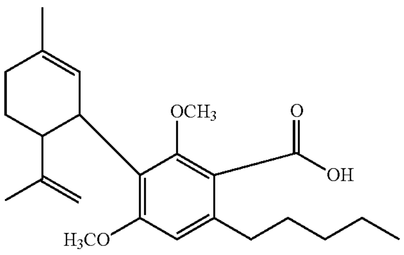

and stereoisomers, and salts thereof.

According to some embodiments, the compound is represented by the structure of Formula (IIb), Formula (IIb)

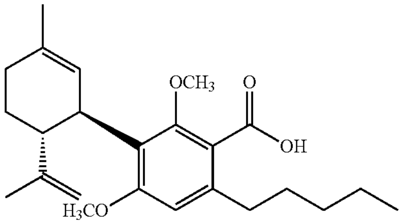

and salts thereof.

According to some embodiments, the compound is represented by the structure of Formula (IIc), Formula (IIc)

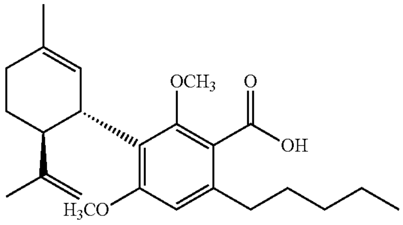

and salts thereof.

According to some embodiments, the compound is represented by the structure of Formula (IId), Formula (IId)

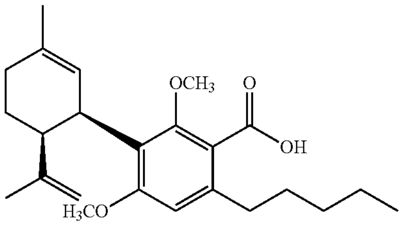

and salts thereof.

According to some embodiments, the compound is represented by the structure of Formula (IIe), Formula (IIe)

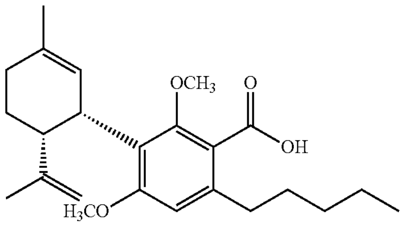

and salts thereof.

According to some embodiments, the compound is represented by the structure of Formula (IIIa), Formula (IIIa)

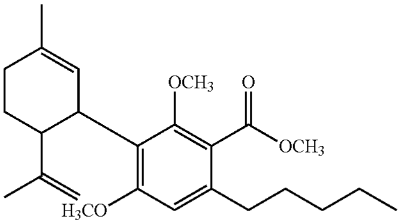

and stereoisomers thereof.

According to some embodiments, the compound is represented by the structure of Formula (IIIb) (designated herein EPM306), Formula (IIIb)

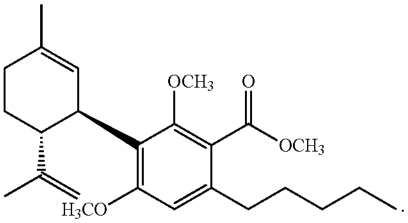

According to some embodiments, the compound is represented by the structure of Formula (IIIc), Formula (IIIc)

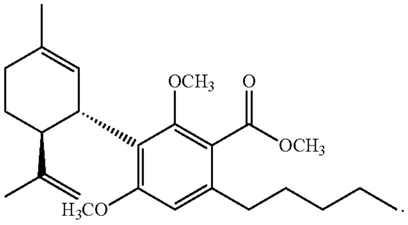

According to some embodiments, the compound is represented by the structure of Formula (IIId), Formula (IIId)

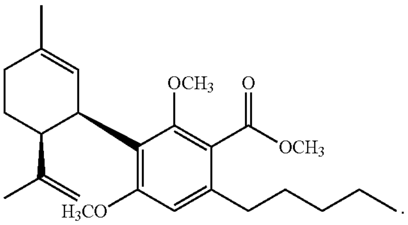

According to some embodiments, the compound is represented by the structure of Formula (IIIe), Formula (IIIe)

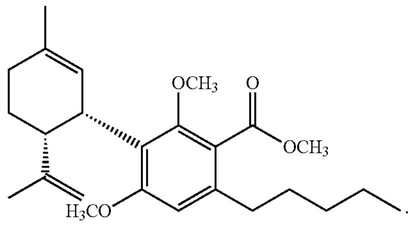

According to another aspect, the present invention provides a pharmaceutical composition comprising a therapeutically effective amount of a compound represented by the structure of Formula (Ia) as defined herein above, and a pharmaceutically acceptable carrier or excipient.

According to some embodiments, the pharmaceutically acceptable carrier or excipient comprises at least one of a binder, a filler, a diluent, a surfactant or emulsifier, a glidant or lubricant, a buffering or pH adjusting agent, a tonicity enhancing agent, a wetting agent, a preservative, an antioxidant, a flavoring agent, a colorant, and a mixture or combinations thereof.

According to some embodiments, the pharmaceutical composition is in a form selected from the group consisting of tablet, pill, capsule, pellets, granules, powder, a wafer, coated or uncoated beads, lozenge, sachet, cachet, elixir, a depot system, a patch, suspension, dispersion, emulsion, solution, syrup, aerosol, oil, ointment, suppository, a gel, and a cream.

According to some embodiments, the pharmaceutical composition is formulated into a dosage form suitable for, oral, intranasal, intravenous, intraarterial, topical, intramuscular, transdermal, intraperitoneal, intrathecal, vaginal, rectal or subcutaneous administration.

According to some embodiments, the present pharmaceutical composition is for use in the treatment of a disease, disorder or symptom amenable to treatment with cannabidiol (CBD).

According to another aspect, the present invention provides a pharmaceutical composition comprising a therapeutically effective amount of a compound represented by the structure of Formula (Ia), for use in the treatment of a disease, disorder or symptom amenable to treatment with cannabidiol (CBD), Formula (Ia)

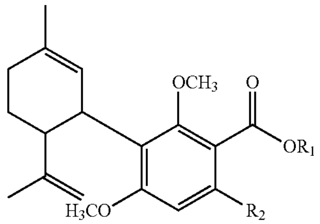

wherein

- $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;
- $R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, $R_1$ is hydrogen. According to some embodiments, $R_1$ is a linear unsubstituted $C_1$-$C_{15}$ alkyl. According to some embodiments, $R_1$ is methyl. According to some embodiments, $R_2$ is a linear unsubstituted $C_1$-$C_{15}$ alkyl. According to some embodiments, $R_2$ is a linear unsubstituted $C_5$ alkyl.

According to some embodiments, the disease, disorder or symptom amenable to treatment with CBD is selected from the group consisting of pain, autoimmune disease, cancer, bacterial infection, impaired neurological function, inflammation, nausea, vomiting, convulsions, low appetite and glaucoma.

According to some embodiments, the pharmaceutical composition is for use in the treatment of pain.

According to some embodiments, the pharmaceutical composition is for use in the treatment of autoimmune disease.

According to some embodiments, the pharmaceutical composition is for use in the treatment of cancer.

According to some embodiments, the pharmaceutical composition is for use in the treatment of bacterial infection.

According to some embodiments, the pharmaceutical composition is for use in the treatment of impaired neurological function.

According to some embodiments, the impaired neurological function is selected from the group consisting of stroke, trauma, Parkinson's Disease, vascular dementia, senile dementia, Alzheimer's disease, mild cognitive impairment, Huntington's Disease, Amyotrophic lateral sclerosis (ALS), epilepsy, multiple sclerosis, and psychiatric disorders.

According to some embodiments, the impaired neurological function is epilepsy.

According to some embodiments, the impaired neurological function is a psychiatric disorder.

According to some embodiments, the psychiatric disorder is selected from the group consisting of depression, anxiety, acute or chronic stress, schizophrenia, panic attacks, ADHD, bipolar disorder, obsessive compulsive disorder and personality disorders.

According to some embodiments, the pharmaceutical composition is for use in the treatment of an inflammation. According to some embodiments, the pharmaceutical composition is for use in treating joint inflammatory diseases and joint degeneration. According to additional embodiments, the pharmaceutical composition is for use in treating respiratory inflammation. According to additional embodiments, the pharmaceutical composition is for use in treating inflammatory bowel disease.

According to some embodiments, the pharmaceutical composition is for use in the treatment of nausea, vomiting or low appetite.

According to some embodiments, the pharmaceutical composition is for use in the treatment of convulsions.

According to some embodiments, the pharmaceutical composition is for use in the treatment of glaucoma.

According to some embodiments, the pharmaceutical composition is for use in the treatment of gastrointestinal diseases or disorders.

According to some embodiments, the disease, disorder or symptom amenable to treatment with CBD is selected from the group consisting of Non-Alcoholic Fatty Liver Disease (NAFLD), chronic kidney disease (CKD), obesity, hyperglycemia, diabetes, metabolic syndrome and/or obesity related diseases.

According to some embodiments, the pharmaceutical composition is for use in the treatment of obesity.

According to some embodiments, the pharmaceutical composition is for use in the treatment of muscular dystrophy.

According to some embodiments, the compound is represented by the structure of Formula (IIa), Formula (IIa)

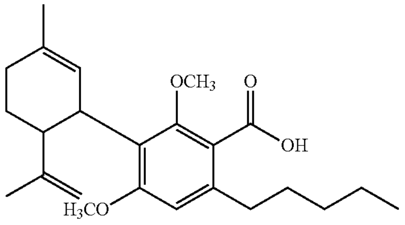

and stereoisomers, and salts thereof.

According to some embodiments, the compound is represented by the structure of Formula (IIIa), Formula (IIIa)

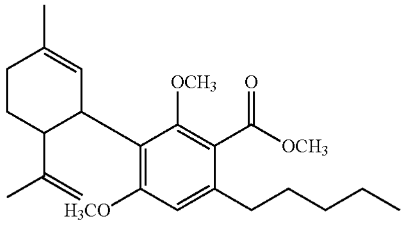

and stereoisomers thereof.

According to some embodiments, the pharmaceutical composition further comprising at least one additional active pharmaceutical ingredient.

According to some embodiments, the additional active pharmaceutical ingredient comprises at least one additional cannabinoid compound.

According to some embodiments, the additional cannabinoid compound is selected from the group consisting of cannabidiol (CBD), cannabigerol (CBG), $\Delta^8$-tetrahydrocannabinol ($\Delta^8$-THC), $\Delta^9$-tetrahydrocannabinol ($\Delta^9$-THC), cannabinol (CBN), $\Delta^9$(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof and combinations thereof.

According to some embodiments, the additional cannabinoid compound comprises a cannabigerolic acid (CBGA) ester represented by Formula (IV), a cannabinolic acid (CBNA) ester represented by Formula (V), a cannabidiolic acid (CBDA) ester represented by Formula (VI), a tetrahydrocannabinolic acid (THCA) ester represented by Formula (VII) or any combination thereof, Formula (IV)

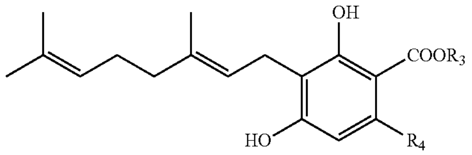

Formula (V)

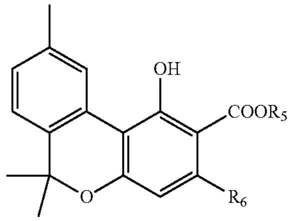

Formula (VI)

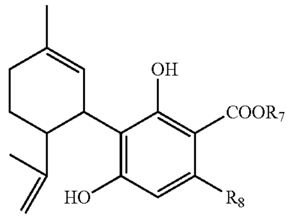

Formula (VII)

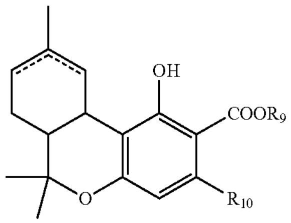

wherein each of $R_5$, $R_6$, $R_7$, $R_8$, $R_9$ and $R_{10}$ is independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

one of the dashed lines in Formula (VII) represents a double bond and the other dashed line represents a single bond;

and stereoisomers, and salts thereof. Each one of the cannabigerolic acid (CBGA) ester represented by Formula (IV), the cannabinolic acid (CBNA) ester represented by Formula (V), the cannabidiolic acid (CBDA) ester represented by Formula (VI), and the tetrahydrocannabinolic acid (THCA) ester represented by Formula (VII) represents a separate embodiment of the present invention.

According to some embodiments, the at least one additional cannabinoid compound is cannabidiolic acid methyl ester (CBDA-ME).

According to some embodiments, the at least one additional cannabinoid compound is present in one or more extracts of a cannabis plant. According to some embodiments, the cannabis plant extract is obtained from a strain selected from the group consisting of *Cannabis sativa, Cannabis indica, Cannabis ruderalis,* a hybrid strain, and combinations thereof. According to some embodiments, the cannabis plant extract is obtained from a strain selected from the group consisting of a high-CBD strain, a high-THC strain, and a combination thereof.

According to some embodiments, the cannabis plant extract comprises at least one cannabinoid selected from the group consisting of cannabidiol (CBD), tetrahydrocannabinol (THC), cannabinol (CBN), cannabigerol (CBG), cannabichromene (CBC), acids thereof and combinations thereof.

According to some embodiments, the cannabis plant extract comprises from about 1 to about 25% (w/w) of CBD. According to some embodiments, the cannabis plant extract comprises about 1% (w/w) of CBD. According to some embodiments, the cannabis plant extract comprises about 10% (w/w) of CBD. According to some embodiments, the cannabis plant extract comprises about 25% (w/w) of CBD.

According to some embodiments, the cannabis plant extract comprises from about 1 to about 25% (w/w) of THC. According to some embodiments, the cannabis plant extract comprises about 1% (w/w) of THC. According to some embodiments, the cannabis plant extract comprises about 10% (w/w) of THC. According to some embodiments, the cannabis plant extract comprises about 25% (w/w) of THC.

According to another aspect, the present invention provides a method of treating a disease, disorder or symptom amenable to treatment with cannabidiol (CBD), the method comprising the step of administering to a subject in need thereof a pharmaceutical composition comprising a therapeutically effective amount of a compound represented by the structure of Formula (Ia) and a pharmaceutically acceptable carrier or excipient, Formula (Ia)

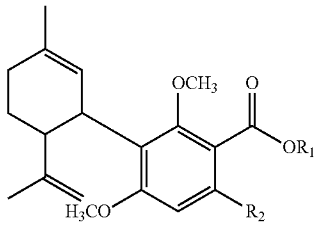

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, wherein $R_1$ is a hydrogen. According to some embodiments, wherein $R_1$ is a linear unsubstituted $C_1$-$C_{15}$ alkyl. According to some embodiments, $R_1$ is $C_1$ alkyl. According to some embodiments, $R_1$ is methyl. According to some embodiments, $R_2$ is a linear unsubstituted $C_1$-$C_{15}$ alkyl. According to some embodiments, wherein $R_2$ is a linear unsubstituted $C_5$ alkyl.

According to some embodiments, the compound is represented by the structure of Formula (IIa), Formula (IIa)

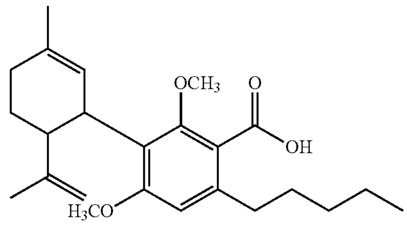

and stereoisomers, and salts thereof.

According to some embodiments, the compound is represented by the structure of Formula (IIIa), Formula (IIIa)

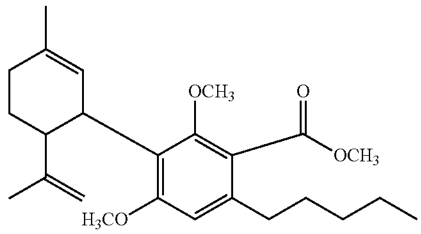

and stereoisomers thereof.

According to some embodiments, the pharmaceutical composition is administered in combination with at least one additional active pharmaceutical ingredient, wherein the at least one additional active pharmaceutical ingredient comprises at least one additional cannabinoid compound. According to some embodiments, the pharmaceutical composition comprises at least one additional active pharmaceutical ingredient, wherein the at least one additional active pharmaceutical ingredient comprises at least one additional cannabinoid compound. According to some embodiments, compound represented by any one of the structure of Formulae (Ia)-(I-e), (IIa)-(II-e) or (IIIa)-(III-e) is administered in combination with at least one additional active pharmaceutical ingredient, wherein the at least one additional active pharmaceutical ingredient comprises at least one additional cannabinoid compound.

According to some embodiments, the additional cannabinoid compound is selected from the group consisting of cannabidiol (CBD), cannabigerol (CBG), $\Delta^8$-tetrahydrocannabinol ($\Delta^8$-THC), $\Delta^9$-tetrahydrocannabinol ($\Delta^9$-THC), cannabinol (CBN), $\Delta^9$(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof and combination thereof.

According to some embodiments, the additional cannabinoid compound comprises a cannabigerolic acid (CBGA) ester represented by Formula (IV), a cannabinolic acid (CBNA) ester represented by Formula (V), a cannabidiolic acid (CBDA) ester represented by Formula (VI), a tetrahydrocannabinolic acid (THCA) ester represented by Formula (VII) or any combination thereof, Formula (IV)

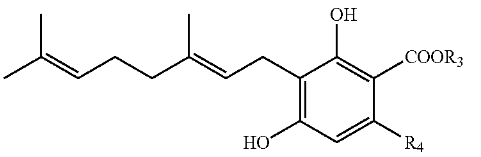

Formula (V)

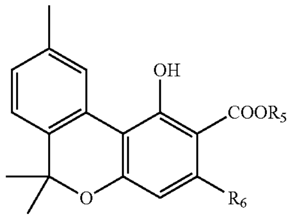

Formula (VI)

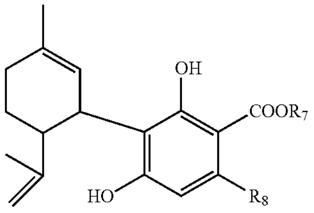

Formula (VII)

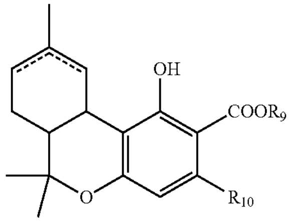

wherein each of $R_1$ and $R_2$ is independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

one of the dashed lines in Formula (VII) represents a double bond and the other dashed line represents a single bond;

and stereoisomers, and salts thereof.

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
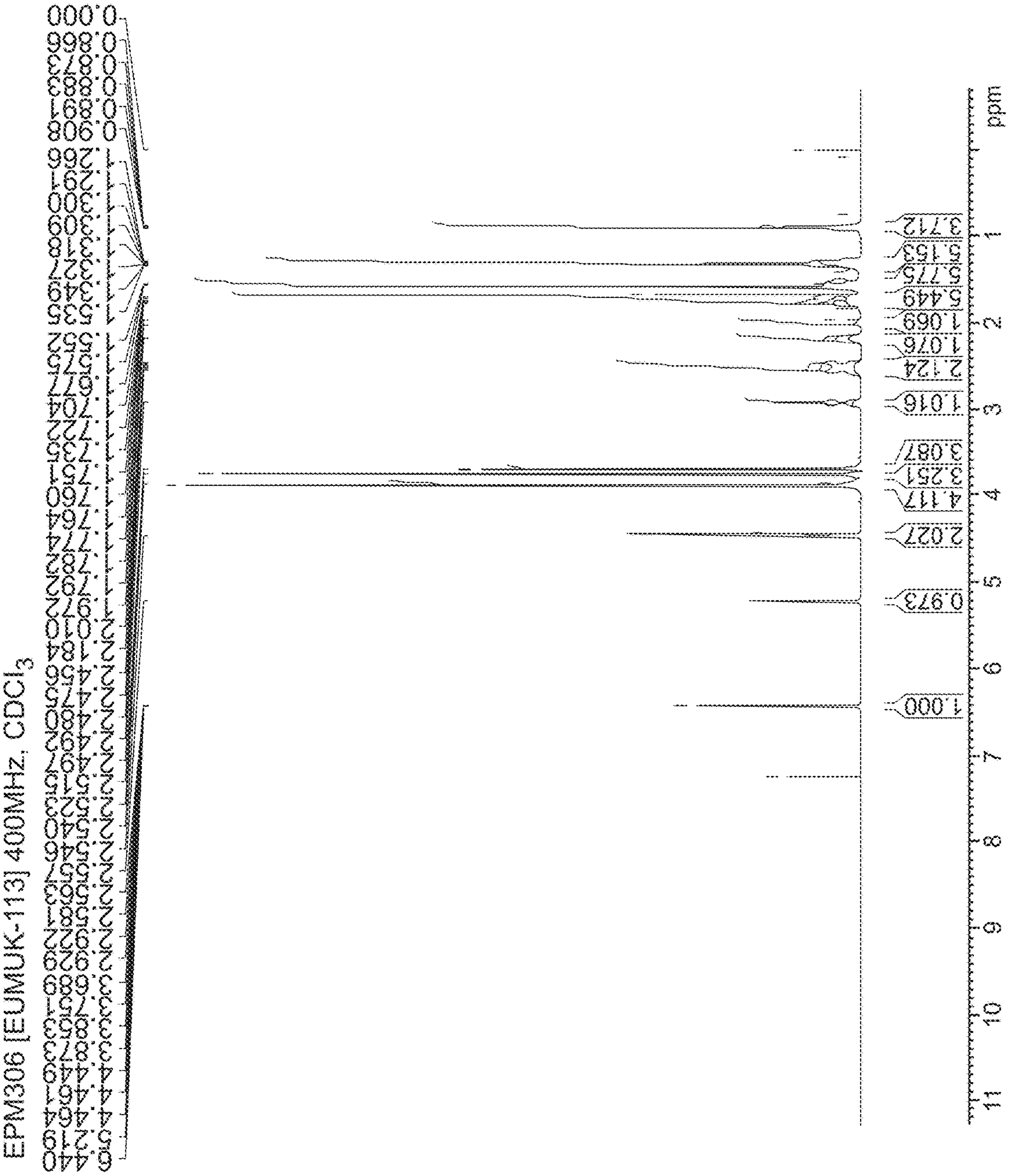
FIGS. 1A-1F represent the $^1$H NMR spectra of EPM306.

The present invention provides novel cannabidiolic acid (CBDA) derivatives including acids and esters, and uses thereof. The present invention further provides pharmaceutical compositions comprising CBDA derivatives, alone or in combination with one or more additional cannabinoid compounds, for use in treating various diseases and disorders and symptoms, including but not limited to, pain, impaired neurological function, inflammation including respiratory inflammation, inflammatory bowel disease and autoimmune diseases, nausea, vomiting, convulsions, low appetite and glaucoma.

According to one aspect, the present invention provides a compound represented by the structure of Formula (Ia), Formula (Ia)

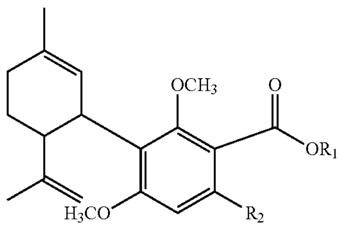

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, the compound is represented by the structure of Formula (Ib), Formula (Ib)

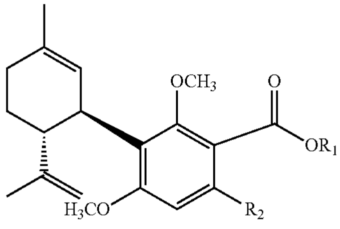

wherein $R_1$ and $R_2$ are defined as for Formula (Ia); and salts thereof.

According to some embodiments, the compound is represented by the structure of Formula (Ic), Formula (Ic)

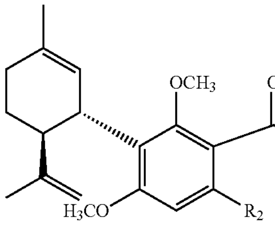

wherein $R_1$ and $R_2$ are defined as for Formula (Ia); and salts thereof.

According to some embodiments, the compound is represented by the structure of Formula (Id), Formula (Id)

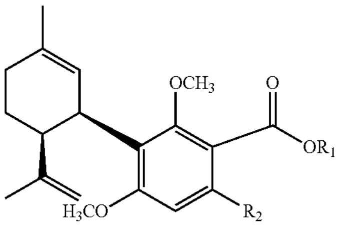

wherein $R_1$ and $R_2$ are defined as for Formula (Ia); and salts thereof.

According to some embodiments, the compound is represented by the structure of Formula (Ie), Formula (Ie)

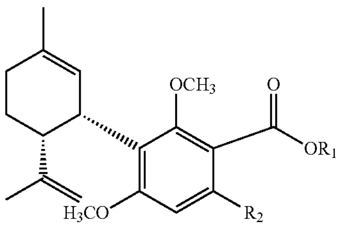

wherein $R_1$ and $R_2$ are defined as for Formula (Ia); and salts thereof.

According to some embodiments, $R_1$ is hydrogen. According to some embodiments, $R_1$ is a linear unsubstituted $C_1$-$C_{15}$ alkyl. According to some embodiments, $R_1$ is a linear unsubstituted $C_2$ alkyl. According to some embodiments, $R_1$ is a linear unsubstituted $C_3$ alkyl. According to some embodiments, $R_1$ is a linear unsubstituted $C_1$-$C_4$ alkyl. According to some embodiments, $R_1$ is a linear unsubstituted $C_5$ alkyl. According to some embodiments, $R_1$ is a linear substituted $C_1$-$C_{15}$ alkyl. According to some embodiments, $R_1$ is a branched unsubstituted $C_1$-$C_{15}$ alkyl. According to some embodiments, $R_1$ is a branched substituted $C_1$-$C_{15}$ alkyl. According to some embodiments, $R_1$ is methyl. According to some embodiments, $R_1$ is a linear unsubstituted $C_2$-$C_{15}$ alkenyl. According to some embodiments, $R_1$ is a linear substituted $C_2$-$C_{15}$ alkenyl. According to some embodiments, $R_1$ is a branched unsubstituted $C_2$-$C_{15}$ alkenyl. According to some embodiments, $R_1$ is a branched substituted $C_2$-$C_{15}$ alkenyl. According to some embodiments, $R_1$ is a linear unsubstituted $C_2$-$C_{15}$ alkynyl. According to some embodiments, $R_1$ is a linear substituted $C_2$-$C_{15}$ alkynyl. According to some embodiments, $R_1$ is a branched unsubstituted $C_2$-$C_{15}$ alkynyl. According to some embodiments, $R_1$ is a branched substituted $C_2$-$C_{15}$ alkynyl.

According to some embodiments, $R_2$ is a linear unsubstituted $C_1$-$C_{15}$ alkyl. According to some embodiments, $R_2$ is a linear substituted $C_1$-$C_{15}$ alkyl. According to some embodiments, $R_2$ is a branched unsubstituted $C_1$-$C_{15}$ alkyl. According to some embodiments, $R_2$ is a branched substituted $C_1$-$C_{15}$ alkyl. According to some embodiments, $R_2$ is a linear unsubstituted $C_2$ alkyl. According to some embodiments, $R_2$ is a linear unsubstituted $C_3$ alkyl. According to some embodiments, $R_2$ is a linear unsubstituted $C_4$ alkyl. According to some embodiments, $R_2$ is a linear unsubstituted $C_5$ alkyl (i.e. n-pentyl). According to some embodiments, $R_2$ is a linear unsubstituted $C_6$ alkyl. According to some embodiments, $R_2$ is a linear unsubstituted $C_2$-$C_{15}$ alkenyl. According to some embodiments, $R_2$ is a linear substituted $C_2$-$C_{15}$ alkenyl. According to some embodiments, $R_2$ is a branched unsubstituted $C_2$-$C_{15}$ alkenyl. According to some embodiments, $R_2$ is a branched substituted $C_2$-$C_{15}$ alkenyl. According to some embodiments, $R_2$ is a linear unsubstituted $C_2$-$C_{15}$ alkynyl. According to some embodiments, $R_2$ is a linear substituted $C_2$-$C_{15}$ alkynyl. According to some embodiments, $R_2$ is a branched unsubstituted $C_2$-$C_{15}$ alkynyl. According to some embodiments, $R_2$ is a branched substituted $C_2$-$C_{15}$ alkynyl.

According to some embodiments, the compound is represented by the structure of Formula (IIa), Formula (IIa)

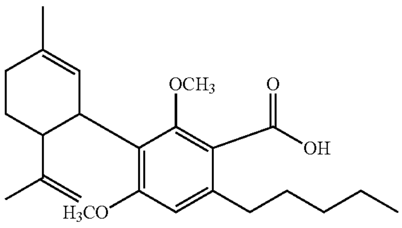

and stereoisomers, and salts thereof.

According to some embodiments, the compound is represented by the structure of Formula (IIb), Formula (IIb)

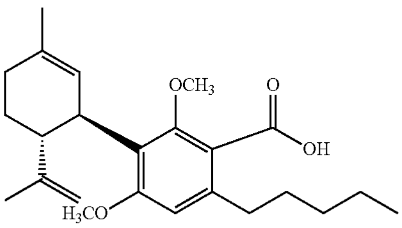

and salts thereof.

According to some embodiments, the compound is represented by the structure of Formula (IIc), Formula (IIc)

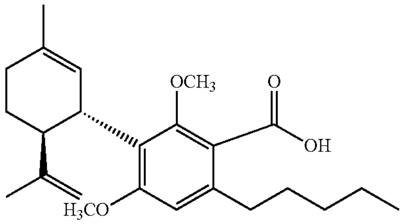

and salts thereof.

According to some embodiments, the compound is represented by the structure of Formula (IId), Formula (IId)

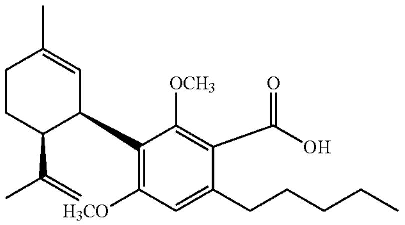

and salts thereof.

According to some embodiments, the compound is represented by the structure of Formula (IIe), Formula (IIe)

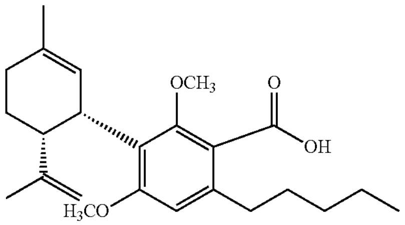

and salts thereof.

According to some embodiments, the compound is represented by the structure of Formula (IIIa), Formula (IIIa)

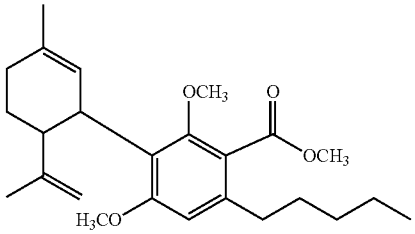

and stereoisomers thereof.

According to some embodiments, the compound is represented by the structure of Formula (IIIb) (designated herein EPM306), Formula (IIIb)

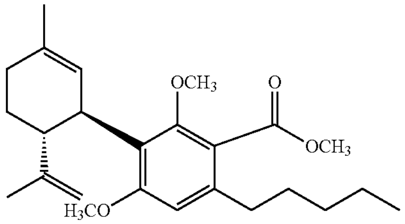

and salts thereof.

According to some embodiments, the compound is represented by the structure of Formula (IIIc), Formula (IIIc)

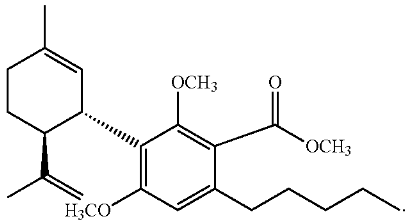

According to some embodiments, the compound is represented by the structure of Formula (IIId), Formula (IIId)

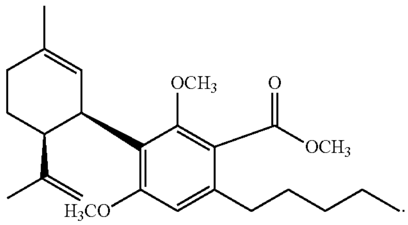

According to some embodiments, the compound is represented by the structure of Formula (IIIe), Formula (IIIe)

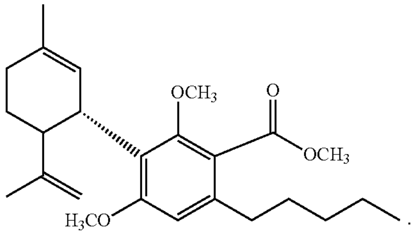

It is to be understood that the compounds provided herein may contain one or more chiral centers. Such chiral centers may each be of either of the (R) or (S) configuration. In case a compound of the invention contains more than one chiral center, each one of those chiral centers may be of the (R) or (S) configuration, independently. Thus, the compounds provided herein may be enantiomerically pure, or be stereoisomeric or diastereomeric mixtures.

An "alkyl" group refers to a saturated aliphatic hydrocarbon, including straight-chain also referred to as linear-chain and branched-chain. In one embodiment, the alkyl group has 1-15 carbons designated here as $C_1$-$C_{15}$-alkyl. In another embodiment, the alkyl group has 2-6 carbons designated here as $C_2$-C6-alkyl. In another embodiment, the alkyl group has 2-4 carbons designated here as $C_2$-$C_4$-alkyl. Each possibility represents a separate embodiment of the invention. The alkyl group may be unsubstituted or substituted by one or more groups selected from the group consisting of hydroxyl, halogen, amino, thiol, phosphate, and combinations thereof. Thus, the phrase "unsubstituted or substituted alkyl" refers to an alkyl group which is either unsubstituted (i.e. it is a hydrocarbon) or to an alkyl substituted with at least one of hydroxyl, halogen, amino, thiol, phosphate, and combinations thereof.

The terms "halo" and "halogen" refer to the fluoro, chloro, bromo or iodo atoms. There can be one or more halogens, which are the same or different.

An "alkenyl" group refers to an aliphatic hydrocarbon group containing at least one carbon-carbon double bond including straight-chain, linear-chain, branched-chain and cyclic alkenyl groups. In one embodiment, the alkenyl group has 2-15 carbon atoms (a $C_2$-$_{15}$ alkenyl). In another embodiment, the alkenyl group has 2-4 carbon atoms in the chain (a $C_2$-$_4$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined herein for alkyl. Thus, the phrase "unsubstituted or substituted alkenyl" refers to an alkenyl group which is either unsubstituted (i.e. it is a hydrocarbon) or to an alkenyl substituted with at least one of hydroxyl, halogen, amino, thiol, phosphate, and combinations thereof.

An "alkynyl" group refers to an aliphatic hydrocarbon group containing at least one carbon-carbon triple bond including straight-chain or linear-chain and branched-chain. In one embodiment, the alkynyl group has 2-15 carbon atoms in the chain (a $C_{2-15}$ alkynyl). In another embodiment, the alkynyl group has 2-4 carbon atoms in the chain (a $C_{2-4}$ alkynyl). Exemplary alkynyl groups include, but are not limited to, ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined herein for alkyl. Thus, the phrase "unsubstituted or substituted alkynyl" refers to an alkynyl group which is either unsubstituted (i.e. it is a hydrocarbon) or to an alkynyl substituted with at least one of hydroxyl, halogen, amino, thiol, phosphate, and combinations thereof.

According to another aspect, the present invention provides a pharmaceutical composition comprising a therapeutically effective amount of a compound represented by the structure of Formula (Ia) and a pharmaceutically acceptable carrier or excipient, Formula (Ia)

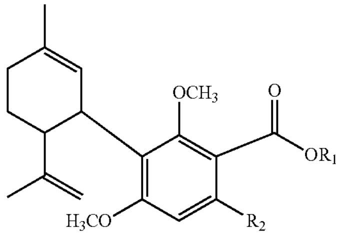

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

The word "cannabinoid" as used herein refers to any compound that interacts with cannabinoid receptors including endocannabinoids (produced naturally in the body by humans and animals), phytocannabinoids (found in cannabis and some other plants), and synthetic cannabinoids (manufactured artificially). The term "cannabinoid acid" refers to the acid form of the above-mentioned cannabinoids.

The word "cannabidiol" refers to cannabidiol (CBD) and CBD derivatives. CBD may be obtained from industrial hemp extract with a trace amount of THC or from cannabis extract using high CBD cannabis cultivars. According to some embodiments, cannabidiol may be obtained from plant extract, or may be prepared synthetically (manufactured artificially), the structure of CBD is presented below:

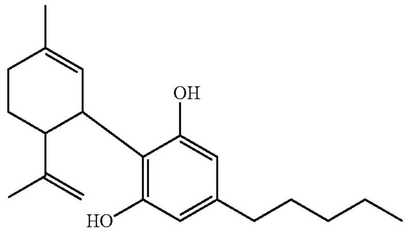

CBD

The abbreviation "CBDA" is used herein to refer to the common cannabidiolic acid, which is the acid form of CBD. The term "cannabidiolic acid ester" or "cannabidiolic ester" refers to various molecules, which are the alkyl or alkenyl ester form of CBDA. The abbreviation "CBDA-ME" is used herein to refer to cannabidiolic acid methyl ester, which is the methyl ester form of CBDA. The structures of CBDA and CBDA-ME are presented below:

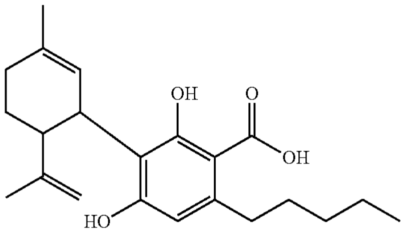

CBDA

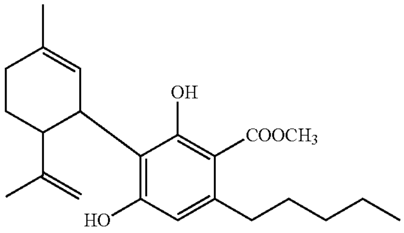

CBDA-ME

The term "cannabidiolic acid derivative" refers to derivatives of CBDA, which are substituted (e.g. alkylated or methylated) at positions 2, 3 and 6 of the aromatic ring by a methoxy group at positions 2 and 6 and by a carboxylic acid at position 3. The term "cannabidiolic acid ester derivative" refers to various molecules, which are the alkyl, alkenyl, or alkynyl form of CBDA derivative as described herein above. The generic chemical structures of CBDA and CBDA ester derivatives are presented below:

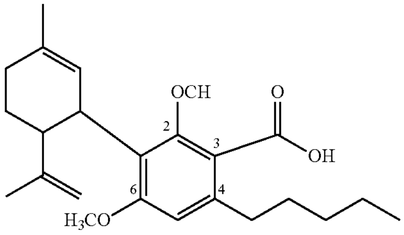

CBDA derivatives

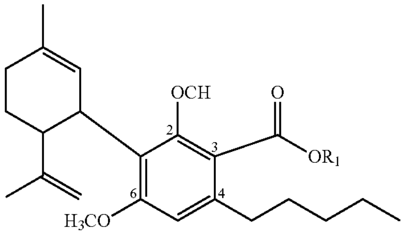

CBDA ester derivatives wherein $R_1$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

It is to be understood that although the common cannabidiolic acid (CBDA) isomers include an n-$C_5H_{11}$ chain at position 4, derivatives of CBDA may include other substituents, in particular alkyl, alkenyl or alkynyl groups. Therefore, the term cannabidiolic acid derivative includes corresponding structures, in which position 4 is substituted by a group, which is either an n-$C_5H_{11}$ or a different chemical group, in particular alkyl, alkenyl or alkynyl groups. The term "cannabidiolic acid" and/or cannabidiolic acid ester" should be interpreted broadly referring to all possible stereo-configurations and salts of the relevant formula.

The present invention thus provides pharmaceutical compositions comprising the compounds disclosed herein and a pharmaceutically acceptable carrier and/or excipient. The compounds of the present invention can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual. Each possibility represents a separate embodiment. The pharmaceutical compositions can be formulated as tablets (including e.g. film-coated tablets), powders, granules, capsules (including soft capsules), orally disintegrating tablets, and sustained-release preparations as is well known in the art. Each possibility represents a separate embodiment.

According to some embodiments, the pharmaceutical composition is formulated into a dosage form suitable for, oral, intranasal, intravenous, intraarterial, topical, intramuscular, transdermal, intraperitoneal, intrathecal, vaginal, rectal or subcutaneous administration.

According to some embodiments, the pharmaceutical composition is formulated as tablet, pill, capsule (e.g. soft or hard gelatin capsule), pellets, granules, powder, a wafer, coated or uncoated beads, lozenge, sachet, cachet, elixir, a depot system, a patch, suspension, dispersion, emulsion, solution, syrup, aerosol, oil, ointment, suppository, a gel, and a cream. Each possibility represents a separate embodiment.

For preparing solid compositions such as tablets, the active pharmaceutical ingredient is mixed with a pharmaceutical carrier or excipient to form a solid pre-formulation composition containing a substantially homogeneous distribution of the compound disclosed herein in the pharmaceutical carrier or excipient.

Any method can be used to prepare the pharmaceutical compositions. For example, solid dosage forms can be prepared by wet granulation, dry granulation, direct compression and the like as is known in the art. The liquid forms in which the compositions disclosed herein may be incorporated, for administration via a route selected from oral, topical or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Each possibility represents a separate embodiment.

According to some embodiments, the composition may be formulated as single-phase aqueous, emulsion or multiple emulsions. According to some embodiments, the composition is formulated as emulsion. These emulsions may be oil-in-water (o/w) emulsions, water-in-oil (w/o) emulsions, or multiple emulsions such as oil-in-water-in-oil (o/w/o) or water-in-oil-in-water (w/o/w). It is understood that the oil phase can comprise silicone oils, non-silicone organic oils, or mixtures thereof. The compositions can comprise two immiscible phases that are reconstituted prior to use. Each possibility represents a separate embodiment.

Compositions for inhalation include solutions and suspensions in pharmaceutically acceptable aqueous or organic solvents, or mixtures thereof, and powders. The liquid or solid compositions may contain suitable pharmaceutically acceptable carriers or excipients as described herein. The compositions may be administered by the oral or nasal respiratory route. Compositions may also be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered, inter alia, orally or nasally, from devices that deliver the formulation in an appropriate manner.

According to some embodiments, the composition is prepared for topical administration, e.g. as an oil, ointment, gel or cream. Adjuvants for topical administration may include, for example, sodium carboxymethylcellulose, polyacrylates, polyoxyethylene-polyoxypropylene-block polymers, polyethylene glycol and wood wax alcohols. The term "gel" as used herein, refers to a substantially dilute cross-linked system, which exhibits little or no flow when in the steady-state having a solid jelly-like matrix. As contemplated herein, gel may comprise hydrogel, organogel, thermosensitive gel, non-thermosensitive gel, and aerogel. Each possibility represents a separate embodiment.

Hydrogels are highly hydrated, macromolecular networks, dispersed in water or other biological fluids. Hydrogels that exhibit the specific property of increased viscosity with increased temperatures are known as thermosensitive (or thermosetting) hydrogels. Such hydrogels have been shown to have easier application combined with longer survival periods at the site of application as compared to non-thermosensitive hydrogels, and are therefore advantageous as sustained-release drug delivery systems. Gel may be characterized by a critical gelation temperature, wherein gelation is effected at the critical gelation temperature or at temperatures above the critical gelation temperature. As used herein, "critical gelation temperature" refers to the lowest temperature at which some gelation of a material is observed (e.g., by increase in shear storage modulus).

According to some embodiments, the pharmaceutical composition can be formulated for local administration into the vagina. In accordance with these embodiments, the compositions may also be embedded in an article or administered using an applicator. Suitable forms for vaginal administration include, but are not limited to, bandage, suppository, pessary, douche, ointment, tablet, tampon, foam, cream, gel, paste, microcapsules, vaginal sponge, vaginal ring, and syringe-like applicator. Each possibility represents a separate embodiment. An optional carrier for vaginal administration comprises a lipid carrier, e.g. fatty acids, glycerin and pharmaceutically acceptable oils.

The pharmaceutical compositions disclosed herein may exhibit release mode which may be immediate release, controlled release or a mixture thereof. Each possibility represents a separate embodiment. "Immediate release" (IR) compositions in the context of the present invention refers to compositions in which the active ingredient is released without delay following administration. "Controlled release" (CR) compositions in the context of the present invention refers to compositions in which the active ingredient is released gradually over a period of time following administration.

Suitable pharmaceutically acceptable carriers or excipients include, but are not limited to, a binder, a filler, a diluent, a surfactant or emulsifier, a glidant or lubricant, buffering or pH adjusting agent, a tonicity enhancing agent, a wetting agent, a preservative, an antioxidant, a flavoring agent, a colorant, and a mixture or combination thereof. Each possibility represents a separate embodiment.

Suitable binders include, but are not limited to, polyvinylpyrrolidone, copovidone, hydroxypropyl methylcellulose, starch, and gelatin. Each possibility represents a separate embodiment.

Suitable fillers include, but are not limited to, sugars such as lactose, sucrose, mannitol or sorbitol and derivatives therefore (e.g. amino sugars), ethylcellulose, microcrystalline cellulose, and silicified microcrystalline cellulose. Each possibility represents a separate embodiment.

Suitable lubricants include, but are not limited to, sodium stearyl fumarate, stearic acid, polyethylene glycol or stearates, such as magnesium stearate. Each possibility represents a separate embodiment.

Suitable diluents include, but are not limited to, dicalcium phosphate dihydrate, sugars, lactose, calcium phosphate, cellulose, kaolin, mannitol, sodium chloride, and dry starch. Each possibility represents a separate embodiment.

Suitable surfactants or emulsifiers include, but are not limited to, polyvinyl alcohol (PVA), polysorbate, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil. Each possibility represents a separate embodiment.

Suitable glidants or lubricants include, but are not limited to, colloidal silicon dioxide, magnesium stearate, talc, and mineral oil. Each possibility represents a separate embodiment.

Suitable buffering or pH adjusting agent include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide. Each possibility represents a separate embodiment.

Suitable tonicity enhancing agents include, but are not limited to, ionic and non-ionic agents such as, alkali metal or alkaline earth metal halides, urea, glycerol, sorbitol, mannitol, propylene glycol, and dextrose. Each possibility represents a separate embodiment.

Suitable wetting agents include, but are not limited to, glycerin, cetyl alcohol, and glycerol monostearate. Each possibility represents a separate embodiment.

Suitable preservatives include, but are not limited to, benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide. Each possibility represents a separate embodiment.

Suitable antioxidants include, but are not limited to, sorbic acid, ascorbic acid, ascorbate, glycine, α-tocopherol, butylated hydroxyanisole (BHA), and butylated hydroxytoluene (BHT). Each possibility represents a separate embodiment.

Suitable flavoring agents include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, eucalyptus, vanilla, citrus oil such as lemon oil, orange oil, grape and grapefruit oil, and fruit essences including apple, peach, pear, strawberry, raspberry, cherry, plum, pineapple, and apricot. Each possibility represents a separate embodiment.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide. Each possibility represents a separate embodiment.

It is contemplated that the compounds include any solvate thereof. The term "solvate" as used herein refers to a physical association of a compound disclosed herein with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. A "hydrate" is a solvate in which the solvent molecule is water.

In embodiments in which the compound is incorporated into a pharmaceutical composition in solid state form, the present disclosure also includes any polymorphs thereof. The term "polymorph" refers to a particular crystalline or amorphous state of a substance, which can be characterized by particular physical properties such as X-ray diffraction, electron diffraction, IR spectra, Raman spectra, melting point, and the like.

Any of the cannabinoids disclosed herein, specifically, the abnormal cannabidiolic acids and their esters, can be prepared synthetically or semi-synthetically.

Natural cannabinoids may be isolated or extracted from a natural source or prepared by synthetic or semi-synthetic means. For example, cannabinoids can be isolated by extraction from cannabis plants. Plants in the cannabis genus include, but are not limited to, *Cannabis sativa, Cannabis ruderalis,* and *Cannabis indica.* Each possibility represents a separate embodiment. These plants are the natural sources of cannabinoids.

According to some embodiments, the pharmaceutical composition further comprising at least one additional active pharmaceutical ingredient.

According to some embodiments, the additional active pharmaceutical ingredient comprises at least one additional cannabinoid compound.

According to some embodiments, the additional cannabinoid compound is selected from the group consisting of cannabidiol (CBD), cannabigerol (CBG), $\Delta^8$-tetrahydrocannabinol ($\Delta^8$-THC), $\Delta^9$-tetrahydrocannabinol ($\Delta^9$-THC), cannabinol (CBN), $\Delta^9$(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof and combinations thereof. Each possibility represents a separate embodiment of the present invention.

According to some embodiments, the additional cannabinoid compound comprises a cannabigerolic acid (CBGA) ester represented by Formula (IV), a cannabinolic acid (CBNA) ester represented by Formula (V), a cannabidiolic acid (CBDA) ester represented by Formula (VI), a tetrahydrocannabinolic acid (THCA) ester represented by Formula (VII) or any combination thereof, Formula (IV)

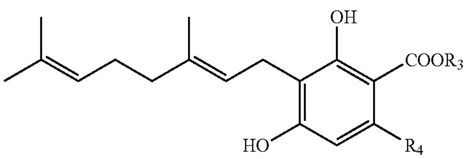

Formula (V)

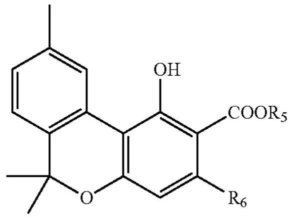

Formula (VI)

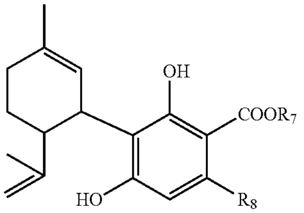

Formula (VII)

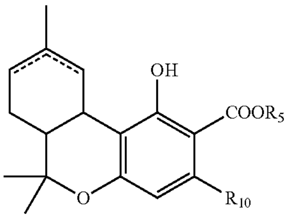

wherein each of $R_5$, $R_6$, $R_7$, $R_8$, $R_9$ and $R_{10}$ is independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

one of the dashed lines in Formula (VII) represents a double bond and the other dashed line represents a single bond;

and stereoisomers, and salts thereof.

According to some embodiments, the additional cannabinoid compound is cannabidiolic acid methyl ester.

According to some embodiments, the additional cannabinoid compound is present in one or more extracts of a cannabis plant. According to some embodiments, the cannabis plant extract is obtained from a strain selected from the group consisting of *Cannabis sativa, Cannabis indica, Cannabis ruderalis,* a hybrid strain, and combinations thereof. According to some embodiments, the cannabis plant extract is obtained from a strain selected from the group consisting of a high-CBD strain, a high-THC strain, and a combination thereof.

According to some embodiments, the cannabis plant extract comprises at least one cannabinoid selected from the group consisting of cannabidiol (CBD), tetrahydrocannabinol (THC), cannabinol (CBN), cannabigerol (CBG), cannabichromene (CBC), acids thereof and combinations thereof.

According to some embodiments, the cannabis plant extract comprises from about 1 to about 25% (w/w) of CBD. According to some embodiments, the cannabis plant extract comprises about 1% (w/w) of CBD. According to some embodiments, the cannabis plant extract comprises about 10% (w/w) of CBD. According to some embodiments, the cannabis plant extract comprises about 25% (w/w) of CBD.

According to some embodiments, the cannabis plant extract comprises from about 1 to about 25% (w/w) of THC. According to some embodiments, the cannabis plant extract comprises about 1% (w/w) of THC. According to some embodiments, the cannabis plant extract comprises about 10% (w/w) of THC. According to some embodiments, the cannabis plant extract comprises about 25% (w/w) of THC.

The term "extract" as used herein refers a product prepared by extraction using physical means (e.g. by comminuting, pressing, heating, pulsed electric field assisted treatments, shear treatments and/or pressure wave treatments), by chemical means (e.g. by treatment with an acid, a base, a solvent) and/or by biochemical means (e.g. by treatment with hydrolytic enzymes, microorganisms). The term refers to a liquid substance obtained through extraction from a given substance, or to a concentrate or essence which is free of, or substantially free of solvent. The term extract may be a single extract obtained from a particular extraction step or series of extraction steps. Extract also may be a combination of extracts obtained from separate extraction steps or separate feedstocks. Such combined extracts are thus also encompassed by the term "extract". Any methods of extraction with suitable solvent are encompassed. Exemplary extraction methods can be found for example in U.S. Pat. No. 6,403,126, the contents of which are incorporated by reference herein. The extract may be obtained from any part of the plant e.g. from leaves, flowers, stems, roots, fruits and seeds. The extract may be aqueous or oily.

According to some embodiments, the cannabis plant extract is formed through contact with a suitable solvent or a combination of solvents. According to some embodiments, the solvent is selected from the group consisting of a polar solvent, a hydrocarbon solvent, carbon dioxide, and a combination thereof.

The term "extract" further refers to a liquid or semi-solid or resinous substance obtained through extraction from plants defined in the present application, i.e. extracts obtained from cannabis plant e.g. *Cannabis sativa, Cannabis indica,* and *Cannabis ruderalis.* In some embodiments, the term refers to a mixture of liquid or semi-solid, resinous substances obtained through extraction from two or more different plants. In some embodiments, the term refers also to a compound purified from the extract. According to some embodiments, the term "extract" has the meaning of a mixture or combination of two or more extracts.

The term "cannabis extract" as used herein refers to one or more plant extracts from the cannabis plant. A cannabis extract contains, in addition to one or more cannabinoids, one or more non-cannabinoid components which are co-extracted with the cannabinoids from the plant material. Their respective ranges in weight will vary according to the starting plant material and the extraction methodology used. Cannabinoid-containing plant extracts may be obtained by various means of extraction of cannabis plant material. Such means include but are not limited to supercritical or sub-critical extraction with $CO_2$, extraction with hot or cold gas and extraction with solvents. In some embodiments, the term refers to a mixture of liquid or semi-solid, resinous substances obtained through extraction from two or more different cannabis species. In some embodiments, the term refers also to a compound purified from the extract. The term "cannabis plant" as used herein, refers to plants of the genus *Cannabis*, including but not limited to *Cannabis sativa, Cannabis indica,* and *Cannabis ruderalis.* According to some embodiments, cannabis plant is a CBD-rich strain of cannabis plant or THC-rich strain of cannabis plant. Each possibility represents a separate embodiment.

The term "hybrid strain" refers to different strains of *Cannabis* which include differing amounts and/or ratios of the various cannabinoid compounds. For example, *Cannabis sativa* typically has a relatively high THC/CBD ratio. Conversely, *Cannabis indica* has a relative low THC/CBD ratio compared to *Cannabis sativa* (although the absolute amount of THC can be higher in *Cannabis indica* than in *Cannabis sativa*).

As used herein the terms "high-CBD strain" and "CBD-rich strain" refer to a strain of cannabis plant which comprises CBD and optionally one or more additional cannabinoids, such as, for example, but not limited to: THC, CBN, and the like. According to some embodiments, CBD is the main component in the high-CBD strain.

As used herein the terms "high-THC strain" and "THC-rich strain" are directed to a strain of cannabis plant which comprises THC and optionally one or more additional cannabinoids, such as, for example, but not limited to: CBD, CBN, and the like. According to some embodiments, THC is the main component in the high-THC strain.

According to another aspect, the present invention provides a pharmaceutical composition comprising a therapeutically effective amount of a compound represented by the structure of Formula (Ia) and a pharmaceutically acceptable carrier or excipient, for use in the treatment of a disease, disorder or symptom amenable to treatment with CBD, Formula (Ia)

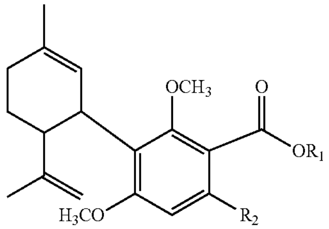

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, the disease, disorder or symptom amenable to treatment with cannabidiol (CBD) is selected from the group consisting of pain, autoimmune disease, cancer, bacterial infection, impaired neurological function, inflammation, nausea, vomiting, convulsions, low appetite and glaucoma. Each possibility represents a separate embodiment of the present invention.

According to some embodiments, the composition disclosed herein is for use in the treatment of pain. According to some embodiments, the composition disclosed herein is for use in the attenuation of pain. According to some embodiments, the composition disclosed herein is for use in the alleviation of pain.

According to some embodiments, the composition disclosed herein is for use in the treatment of autoimmune disease.

According to some embodiments, the composition disclosed herein is for use in the treatment of cancer. According to some embodiments, the composition disclosed herein is for use as an anti-tumor agent.

According to some embodiments, the composition disclosed herein is for use in the treatment of bacterial infection. According to some embodiments, the composition disclosed herein is for use as an anti-bacterial agent.

According to some embodiments, the composition disclosed herein is for use in the treatment of impaired neurological function.

According to some embodiments, the composition disclosed herein is for use in the treatment of impaired neurological function selected from the group consisting of stroke, trauma, Parkinson's disease, vascular dementia, senile dementia, Alzheimer's disease, mild cognitive impairment, Huntington's Disease, Amyotrophic lateral sclerosis (ALS), epilepsy, multiple sclerosis, and psychiatric disorders. Each possibility represents a separate embodiment of the present invention.

According to some embodiments, the impaired neurological function is epilepsy.

According to some embodiments, the composition disclosed herein is for use in the treatment of psychiatric disorders. According to some embodiments, the psychiatric disorder is selected from the group consisting of depression, anxiety, acute or chronic stress, schizophrenia, panic attacks, ADHD, bipolar disorder, obsessive compulsive disorder or personality disorders. Each possibility represents a separate embodiment of the present invention.

According to some embodiments, the composition disclosed herein is for use in the treatment of depression. According to some embodiments, the composition disclosed herein is for use in the treatment of anxiety. According to some embodiments, the composition disclosed herein is for use in the treatment of acute or chronic stress. According to some embodiments, the composition disclosed herein is for use in the treatment of schizophrenia. According to some embodiments, the composition disclosed herein is for use in the treatment of panic attacks. According to some embodiments, the composition disclosed herein is for use in the treatment of ADHD. According to some embodiments, the composition disclosed herein is for use in the treatment of bipolar disorder. According to some embodiments, the composition disclosed herein is for use in the treatment of obsessive-compulsive disorder.

According to some embodiments, the composition disclosed herein is for use in the treatment of inflammation.

According to some embodiments, the composition disclosed herein is for use in treating joint inflammatory diseases and joint degeneration. According to additional embodiments, the pharmaceutical composition is for use in treating respiratory inflammation. According to additional embodiments, the composition disclosed herein is for use in treating inflammatory bowel disease.

According to some embodiments, the inflammation is respiratory inflammation.

According to some embodiments, the respiratory inflammation is acute respiratory inflammation.

The respiratory inflammation can be associated with a disease or disorder including, but not limited to, asthma, chronic obstructive airway disorder, chronic obstructive pulmonary disease (COPD), pneumonia, respiratory syncytial viral infection, bronchitis, bronchiolitis, idiopathic pulmonary fibrosis, cystic fibrosis, acute respiratory distress syndrome (ARDS), bronchopulmonary dysplasia, occupational respiratory disease, particulate exposure, pleurisy, emphysema, and pulmonary edema.

According to some embodiments, the respiratory inflammation is chronic respiratory inflammation. According to certain embodiments, the respiratory inflammation is pneumonitis. According to certain embodiments, the respiratory inflammation is asthma. According to certain embodiments, the respiratory inflammation is COPD.

According to some embodiments, the respiratory inflammation is caused by a pathogen. According to certain embodiments, the respiratory inflammation is caused by a pathogen selected from the group consisting of bacteria, viruses, parasites and fungi.

According to some embodiments, the respiratory inflammation is caused by a virus. According to additional embodiments, the respiratory inflammation is caused by Severe acute respiratory syndrome (SARS) virus. According to additional embodiments, the respiratory inflammation is caused by SARS-CoV-2 (Covid-19).

According to some embodiments, the composition disclosed herein is for use as a neuroprotective agent. According to some embodiments, the composition disclosed herein is for use in treating multiple sclerosis.

According to some embodiments, the composition disclosed herein is for use in treating cancer.

According to some embodiments, the composition disclosed herein is for use in the treatment of a symptom selected from the group consisting of nausea, vomiting and low appetite. According to some embodiments, the composition disclosed herein is for use in the treatment of nausea. According to some embodiments, the composition disclosed herein is for use in the treatment of vomiting. According to some embodiments, the composition disclosed herein is for use in the treatment of low appetite.

According to some embodiments, the composition disclosed herein is for use in the treatment of convulsions.

According to some embodiments, the composition disclosed herein is for use in the treatment of glaucoma.

According to some embodiments, the composition disclosed herein is for use in the treatment of gastrointestinal diseases or disorders.

According to some embodiments, the composition disclosed herein is for use in the treatment of Non-Alcoholic Fatty Liver Disease (NAFLD), chronic kidney disease (CKD), obesity, hyperglycemia, diabetes, metabolic syndrome and/or obesity related diseases.

According to some embodiments, the composition disclosed herein is for use in the treatment of obesity.

According to some embodiments, the composition disclosed herein is for use in the treatment of muscular dystrophy.

According to another aspect, the present invention provides a method of treating a disease, disorder or symptom amenable to treatment with cannabidiol (CBD), the method comprising administering to a subject in need thereof a pharmaceutical composition comprising a therapeutically effective amount of a compound represented by the structure of Formula (Ia) and a pharmaceutically acceptable carrier or excipient, Formula (Ia)

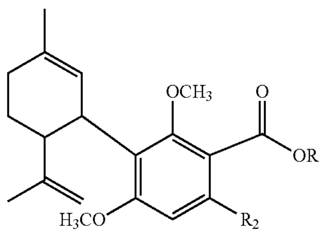

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

According to some embodiments, the method of treating, a disease, disorder or symptom is selected from the group consisting of impaired neurological function, inflammation, nausea, vomiting, convulsions, low appetite, and glaucoma, the method comprising administering to a subject in need thereof the pharmaceutical composition disclosed herein.

According to some embodiments, the impaired neurological function is selected from the group consisting of stroke, trauma, Parkinson's disease, vascular dementia, senile dementia, Alzheimer' s disease, mild cognitive impairment, Huntington's Disease, Amyotrophic lateral sclerosis (ALS), epilepsy, multiple sclerosis, and psychiatric disorders.

According to some embodiments, there is provided a method of treating, attenuating or alleviating pain, the method comprising administering to a subject in need thereof the pharmaceutical composition disclosed herein.

According to some embodiments, there is provided a method of treating, attenuating or alleviating pain, the method comprising administering to a subject in need thereof a pharmaceutical composition comprising a therapeutically effective amount of a compound represented by the structure of Formula (Ia) as described herein above, and a pharmaceutically acceptable carrier or excipient.

According to some embodiments, the pharmaceutical composition is administered in combination with at least one additional active pharmaceutical ingredient as described herein.

Other suitable additional active pharmaceutical ingredients include agents for pain relief such as non-steroidal anti-inflammatory agents (NSAIDs). Suitable NSAIDs include, but are not limited to, acetyl salicylic acid, indometacin, sulindac, phenylbutazone, diclofenac, fentiazac, ketorolac, piroxicam, tenoxicam, mecoxicam, meloxicam, cinnoxicam, ibufenac, ibuprofen, naproxen, ketoprofen, nabumetone, niflumic acid, nimesulide, and pharmaceutically acceptable salts thereof. Each possibility represents a separate embodiment of the invention.

A group of NSAIDs within the scope of the present invention are Cox-2 inhibitors. Cox-2 inhibitors suitable for use in the combinations of the present invention include, but are not limited to, (4-(4-cyclohexyl-2-methyloxazol-5-yl)-2-fluorobenzenesulfonamide), 5-chloro-3-(4-(methylsulfonyl)phenyl)-2-(methyl-5-pyridinyl)pyridine, 2-(3,5-difluorophenyl)-3-4 (methylsulfonyl)phenyl)-2-cyclopenten-1-one, 4-[5-(4-methylphenyl)-3-(trifluoromethyl)-1H-pyrazol-1-yl]-benzene sulfonamide, rofecoxib, (4-(4-methylsulfonyl)phenyl]-3-phenyl-2(5H)-furanone), 4-(5-methyl-3-phenylisoxazol-4-yl)benzenesulfonamide, N-[[4-(5-methyl-3-phenylisoxazol-4yl]phenyl]sulfonyl] propanamide, 4-[5-(4-chlorophenyl)-3-(trifluoromethyl)-1H-pyrazole-1-yl]benzenesulfonamide, N-(2, 3-dihydro-1, 1-dioxido-6-phenoxy-1, 2-benzisothiazol-5-yl) methanesulfonamide, 6-[[5-(4-chlorobenzoyl)-1,4-dimethyl-1H-pyrrol-2-yl]methyl]-3(2H)-pyridazinone, N-(4-nitro-2-phenoxyphenyl) methanesulfonamide, 3-(3,4-difluorophenoxy)-5,5-dimethyl-4-[4-(methylsulfonyl) phenyl]-2 (SH)-furanone, N-[6-[(2, 4-difluorophenyl) thio]-2, 3-dihydro-1-oxo-1H-inden-5-yl] methanesulfonamide, 3-(4-chlorophenyl)-4-[-4-(methylsulfonyl) phenyl]-2 (3H)-oxazolone, 4-[3-(4-fluorophenyl)-2,3-dihydro-2-oxo-4-oxazolyl] benzenesulfonamide, 3-[4-(methylsulfonyl) phenyll-2-phonyl-2-cyclopenten-1-one, 4-(2-methyl-4-phenyl-5-oxazolyl)benzenesulfonamide, 3-(4-fluorophenyl)-4-[4-(methylsulfonyl) phenyl]-2 (3H)-oxazolone, 5-(4-fluorophenyl)-1-[4-(methylsulfonyl) phenyl]-3-(trifluoromethyl)-1H-pyrazole, 4-[5-phenyl)-3-(trifluoromethyl)-1H-pyrazol-1-yl)benzenesulfonamide, 4-[1-phenyl-3-(trifluoromethyl)-1H-pyrazol-5-yl] benzenesulfonamide, 4-[5-(4-fluorophenyl)-3-(trifluoromethyl)-1H-pyrazol-1-yl] benzenesulfonamide, N-[2-(cyclohexyloxy)-4-nitrophenyl] methanesulfonamide, N-[6-(2, 4-difluorophenoxy)-2, 3-dihydro-1-oxo-1H-inden-5-yl] methanesulfonamide, 3-(4-chlorophenoxy-4-[(methylsulfonyl)amino]benzenesulfonamide, 3-(4-chlorophenoxy-4-[(methylsulfonyl)amino]benzenesulfonamide, 3-[(I-methyl-IH-imidzaol-2-yl) thio]-4 [(methylsulfonyl) amino] benzenesulfonamide, 5,5-dimethyl-4-[4-(methylsulfonyl) phenyl]-3-phenoxy-2(5H)-furanone, N-[6-[(4-ethyl-2-thiazolyl) thio]-1, 3-dihydro-1-oxo-5-isobenzofuranyl] methanesulfonamide, 3-[(2,4-dichlorophenyl)thio]-4-[(methylsulfonyl)amino]benzenesulfonamide, 1-fluoro-4-[2-[4-(methylsulfonyl) phenyl] cyclopenten-1-yl] benzene, 4-[5-(4-chlorophenyl)-3-(difluoromethyl)-1H-pyrazol-1-yl] benzenesulfonamide, 3-[1-[4-(methylsulfonyl)phenyl]-4-(trifluoromethyl)-1H-imidazol-2-yl] pyridine, 4-[2-(3-pyridinyll)-4-(trifluoromethyl)-1H-imidazol-1-yl] benzenesulfonamide, 4-[5-(hydroxymethyl)-3-phenylisoxazol-4-yl]benzenesulfonamide, 4-[3-(4-chlorophenyl)-2,3-dihydro-2-oxo-4-oxazolyl] benzenesulfonamide, 4-[5-(difluoromethyl)-3-phenylisoxazol-4-yl] benzenesulfonamide, [1, 1':2', 1"-terphenyl]-4-sulfonamide, 4-(methylsulfonyl)-1,1', 2], 1"-terpheynyl, 4-(2-phenyl-3-pyridinyl)benzenesulfonamide, N-[3-(fonnylamino)-4-oxo-6-phenoxy-4H-1-benzopyran-7-yl] methanesulfonamide, darbufelone, celecoxib, rofecoxib, parecoxib, and valdecoxib. Each possibility represents a separate embodiment of the invention. Exemplary Cox-2 inhibitors include, but are not limited to, celecoxib, rofecoxib, parecoxib and valdecoxib. Each possibility represents a separate embodiment of the invention.

According to some embodiments, there is provided a method of treating psychiatric disorders, the method comprising administering to a subject in need thereof the pharmaceutical composition disclosed herein.

According to some embodiments, there is provided a method of treating psychiatric disorders, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, the pharmaceutical composition is administered in combination with at least one additional active pharmaceutical ingredient as described herein.

According to some embodiments, there is provided a method of treating impaired neurological function, the method comprising administering to a subject in need thereof the pharmaceutical composition disclosed herein.

According to some embodiments, there is provided a method of treating epilepsy comprising administering to a subject in need thereof the pharmaceutical composition disclosed herein.

According to some embodiments, there is provided a method of treating impaired neurological function, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, there is provided a method of treating epilepsy, the method comprising administering to a subject in need thereof a pharmaceutical composition comprising a therapeutically effective amount of a compound ester represented by the structure of Formula (Ia) as described herein, and a pharmaceutically acceptable carrier or excipient.

According to some embodiments, the pharmaceutical composition is administered in combination with at least one additional active pharmaceutical ingredient as described herein.

According to some embodiments, there is provided a method of treating inflammation, the method comprising administering to a subject in need thereof the pharmaceutical composition disclosed herein.

According to some embodiments, there is provided a method of treating inflammation, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, there is provided a method of treating joint inflammatory diseases and joint degeneration, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, there is provided a method of treating respiratory inflammation, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, there is provided a method of treating inflammatory bowel disease, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, the pharmaceutical composition is administered in combination with at least one additional active pharmaceutical ingredient as described herein.

According to some embodiments, there is provided a method of treating a symptom selected from the group consisting of nausea, vomiting and low appetite, the method comprising administering to a subject in need thereof the pharmaceutical composition disclosed herein. Each possibility represents a separate embodiment of the present invention.

According to some embodiments, there is provided a method of treating a symptom selected from the group consisting of nausea, vomiting and low appetite, the method comprising administering to a subject in need thereof a pharmaceutical composition comprising a therapeutically effective amount of a compound represented by the structure of Formula (Ia) as described herein, and a pharmaceutically acceptable carrier or excipient. Each possibility represents a separate embodiment of the present invention.

According to some embodiments, the pharmaceutical composition is administered in combination with at least one additional active pharmaceutical ingredient as described herein. According to some embodiments, the symptom is nausea. According to some embodiments, the symptom is vomiting. According to some embodiments, the symptom is low appetite.

According to some embodiments, there is provided a method of treating convulsions, the method comprising administering to a subject in need thereof the pharmaceutical composition disclosed herein.

According to some embodiments, there is provided a method of treating convulsions, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, the pharmaceutical composition is administered in combination with at least one additional active pharmaceutical ingredient as described herein.

According to some embodiments, there is provided a method of treating glaucoma, the method comprising administering to a subject in need thereof the pharmaceutical composition disclosed herein.

According to some embodiments, there is provided a method of treating glaucoma, the method comprising administering to a subject in need thereof a pharmaceutical composition comprising a therapeutically effective amount of a compound represented by the structure of Formula (Ia) as described herein, and a pharmaceutically acceptable carrier or excipient.

According to some embodiments, the pharmaceutical composition is administered in combination with at least one additional active pharmaceutical ingredient as described herein.

Although the pharmaceutical composition comprising the compound of the present invention may be administered as the single therapeutic agent for the treatment of diseases or disorders described herein, combination therapy including co-administration of one or more additional active pharmaceutical ingredients is within the scope of the present invention. Co-administration of the compound of the present invention with one or more therapeutic agents may take place sequentially in any order, simultaneously or a combination thereof. For example, administration of the compound of the present invention can take place prior to, after or at the same time as the administration of the additional therapeutic agent(s). For example, a total treatment period can be decided for the compound of the present invention. The additional agent(s) can be administered prior to the onset of treatment with the compound of the present invention or following treatment with the compound of the present invention. In addition, the additional agent(s) can be administered during the period of administering the compound of the present invention but does not need to occur over the entire treatment period. In another embodiment, the treatment regimen includes pre-treatment with one agent, followed by the addition of the other agent or agents. Alternating sequences of administration are also contemplated. Alternating administration includes administration of the compound of the present invention, followed by the additional agent, followed by the compound of the present invention, etc. The aforementioned sequences can also be administrated in several cycles wherein each cycle may be similar or different with each possibility representing a separate embodiment. The therapeutic efficacy of the combination of the compound of the present invention and the additional agent(s) is at least additive. In some embodiments, the therapeutic efficacy is synergistic, namely the overall dose of each of the components may be lower, thus resulting in significantly lower side effects experienced by the subject, while a sufficient desirable therapeutic effect is nonetheless achieved. When combination therapy is involved, the compound of the present invention and the additional therapeutic agent(s) may he provided in a single dosage form such as a fixed-dose combination or in separate compositions intended for simultaneous administration.

The precise dose to be employed in the pharmaceutical composition disclosed herein will depend on the route of administration, and the seriousness of the disease, and should be decided according to the judgment of the practitioner and each patient's circumstances. An optional dosage will be within the range of about 0.01-1000 mg/kg of body weight, about 0.1 mg/kg to 100 mg/kg, about 1 mg/kg to 100 mg/kg, about 10 mg/kg to 75 mg/kg, about 0.1 to 1 mg/kg etc., including each value within the specified range.

According to some embodiments, the composition comprises the compound of the present invention at a concentration of between 10 to 200 mg/ml.

The administration schedule will depend on several factors such as the severity and progression of the disease, disorder or symptom. For example, the compositions of the invention can be taken once-daily, twice-daily, thrice daily, once-weekly or once-monthly. In addition, the administration can be continuous, i.e., every day, or intermittently. The terms "intermittent" or "intermittently" as used herein means stopping and starting at either regular or irregular intervals. For example, intermittent administration can be administration one to six days per week or it may mean administration in cycles (e.g. daily administration for two to eight consecutive weeks, then a rest period with no administration for up to one week) or it may mean administration on alternate days. The effectiveness of said compositions could enable a shortened period of treatment with superior results.

"A therapeutically effective amount" as used herein refers to an amount of an agent which is effective, upon single or multiple dose administration to the subject in providing a therapeutic benefit to the subject. In additional embodiments, the compounds of the present invention are used for the preparation of a medicament for treating any one of the diseases, disorders, conditions or symptoms disclosed herein.

The following examples describe specific aspects of the invention to illustrate the invention and provide a description of the present methods for those skilled in the art. It should be noted that the term "and" or the term "or" is generally employed in its sense including "and/or" unless the context clearly dictates otherwise. As used herein, the term "about" is meant to encompass variations of ±10%.

EXAMPLES

Synthesis

EPM306 is provided as an example of CBDA ester derivative obtainable by the following processes. The synthesis described in Examples 1 to 3 is directed to preparing EPM306 in three steps by first carboxylating of a commercial cannabidiol (CBD) to form cannabidiolic acid (CBDA), following by performing an esterification of the CBDA and then performing methylation reactions of the hydroxyl groups.

Example 1. Synthesis of Cannabidiolic Acid (CBDA)

The preparation process described in the PCT application WO 2018/235079 was applied. A mixture of cannabidiol (CBD, 314 mg, 1 mmol) and 2 molar solution of magnesium methyl carbonate (MMC/2M, 1.5 ml, 3 mmol) in dimethylformamide (DMF) was heated at 130° C. for 3 hours. Then the reaction was cooled to 0° C., acidified with 10% hydrochloric acid and extracted with ether. The organic layer was washed with saline, dried over the drying agent magnesium sulfate ($MgSO_4$) and then evaporated. The crude compound was then cleaned by column chromatography (20% ether-petroleum ether).

Example 2. Synthesis of Cannabidiolic Acid Methyl Ester (CBDA-ME)

The preparation process described in the PCT application WO 2018/235079 was applied. To a solution of cannabidiolic acid (CBDA) (175 mg, 0.488 mmol) in 2.5 ml dichloromethane ($CH_2Cl_2$), was added 0.02 ml of methanol ($CH_3OH$, 0.488 mmol) and 7.2 mg of 4-pyrrolidinopyridine (0.048 mmol). The reaction was stirred for 5 minutes at room temperature followed by the addition of the coupling agent, N,N' Dicyclohexylcarbodiimide (DCC) (121 mg, 0.585 mmol) and stirred overnight. Then the solvent was evaporated and the crude mixture acidified with 5% hydrochloric acid and extracted with dichloromethane ($CH_2Cl_2$). The organic layer was washed with saturated aqueous sodium bicarbonate ($NaHCO_3$), dried over the drying agent magnesium sulfate ($MgSO_4$) and then evaporated. The crude compound was then cleaned by column chromatography (2% ether-petroleum ether).

$^1$H-NMR spectra were obtained using a Bruker AMX 300 MHz apparatus using the deuterated DMSO. Thin-layer chromatography (TLC) was run on silica gel 60F254 plates (Merck). Column chromatography was performed on silica gel 60 Å (Merck). Compounds were located using a UV lamp at 254 nm.

$^1H$ NMR (300 MHz, $((CD_3)_2SO)$) δ 6.18 (1H, s, Ar), 5.07 (1H, s), 4.44 (1H, s), 4.41 (1H, s), 3.82 (3H, s), 3.35 (1H, m), 2.66 (1H, m), 2.49 (2H, t), 2.09 (1H, b), 1.95 (3H, s),1.71-1.05 (12, ms), 0.86 (3H, t).

Example 3. Synthesis of EPM306

Figure 1B:
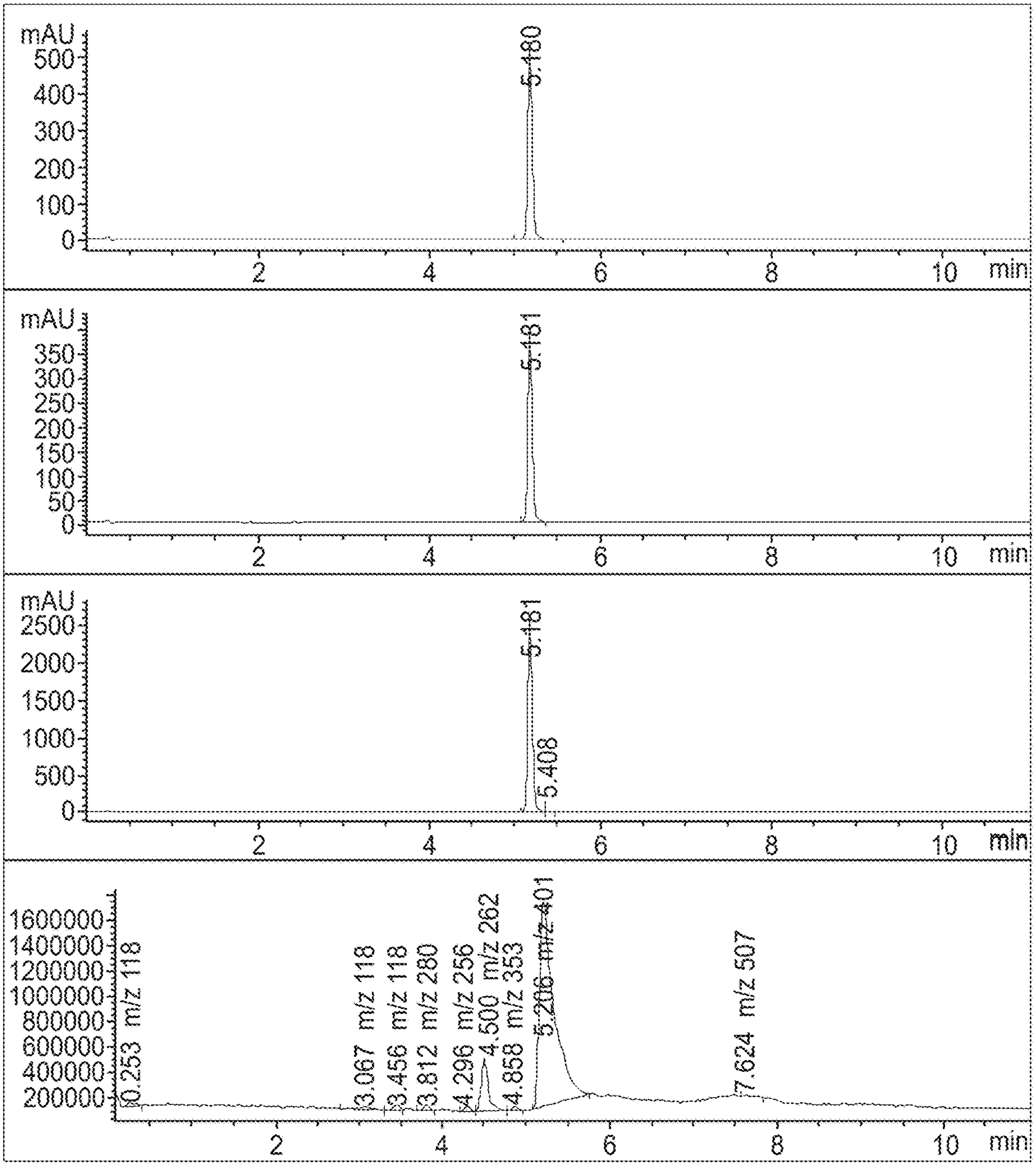
Figure 1C:
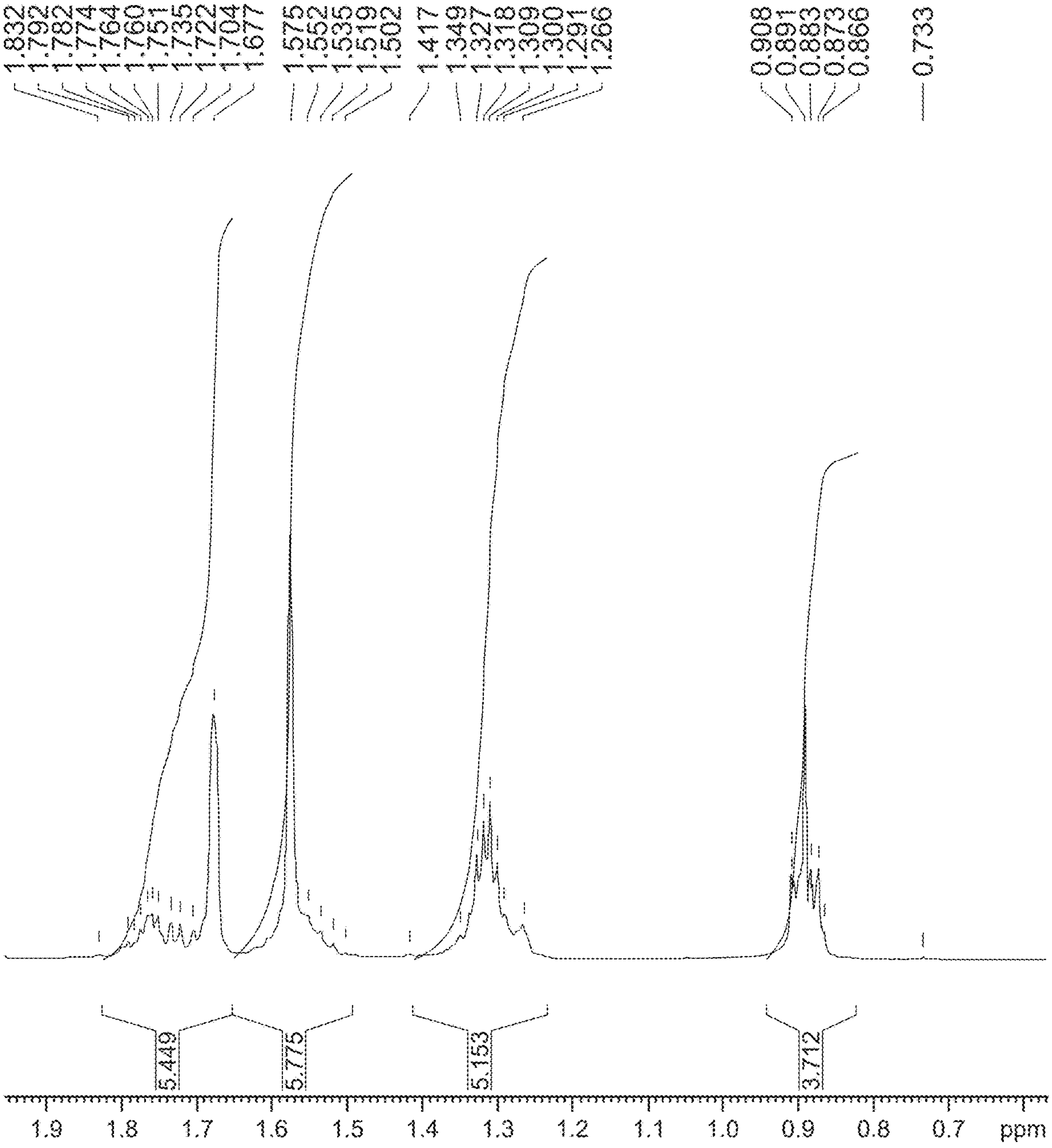
Figure 1D:
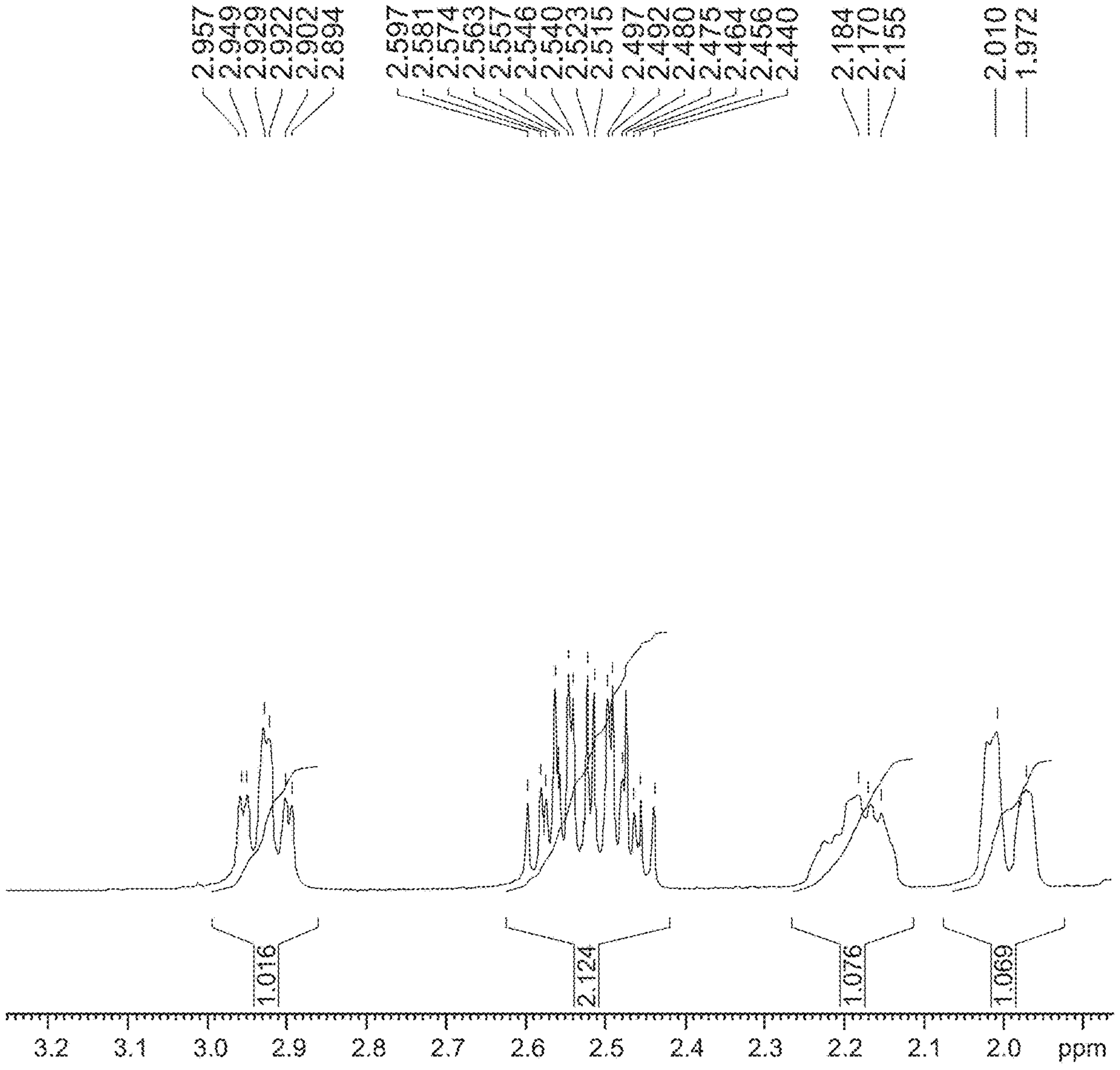
Figure 1E:
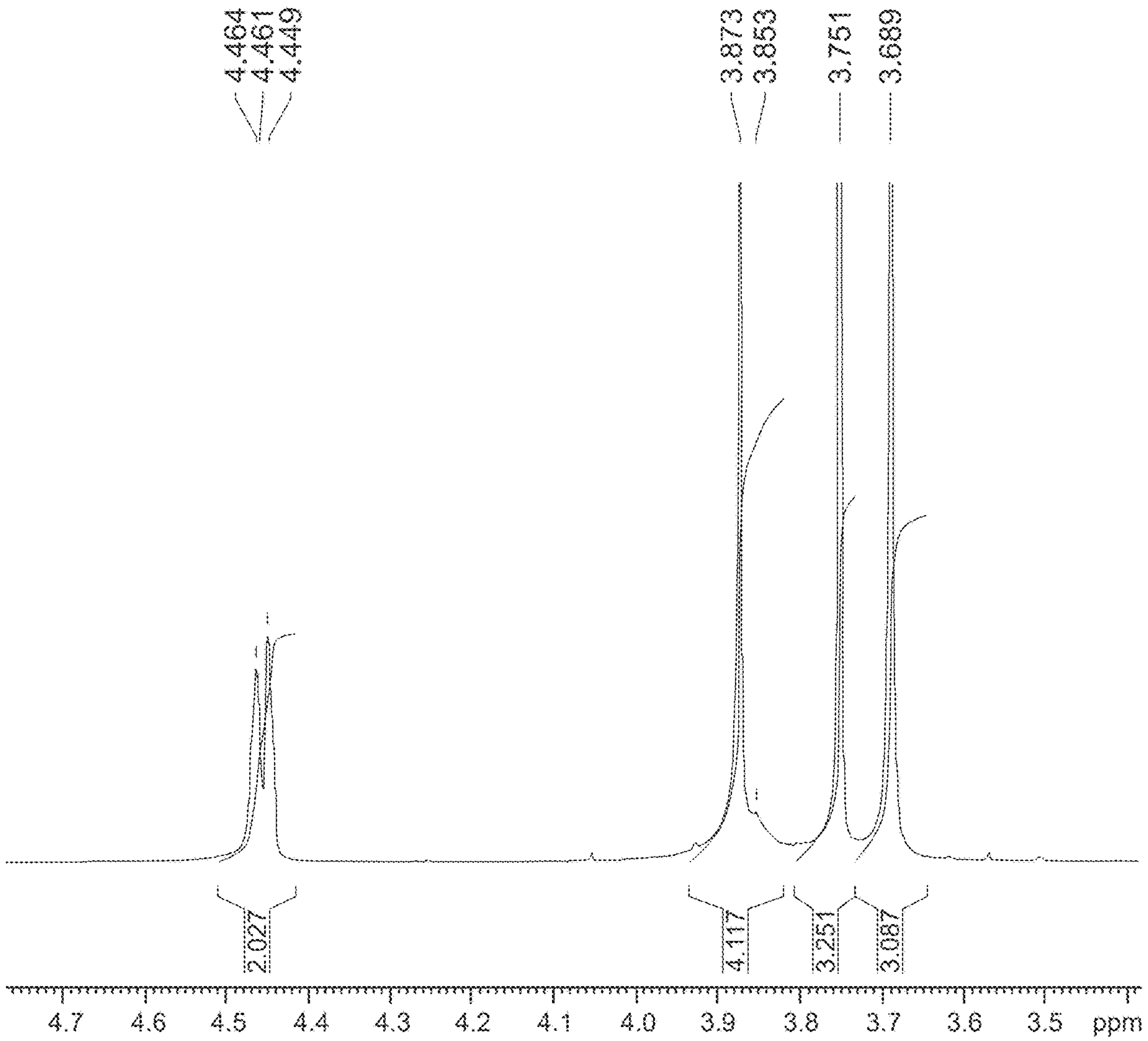
Figure 1F:
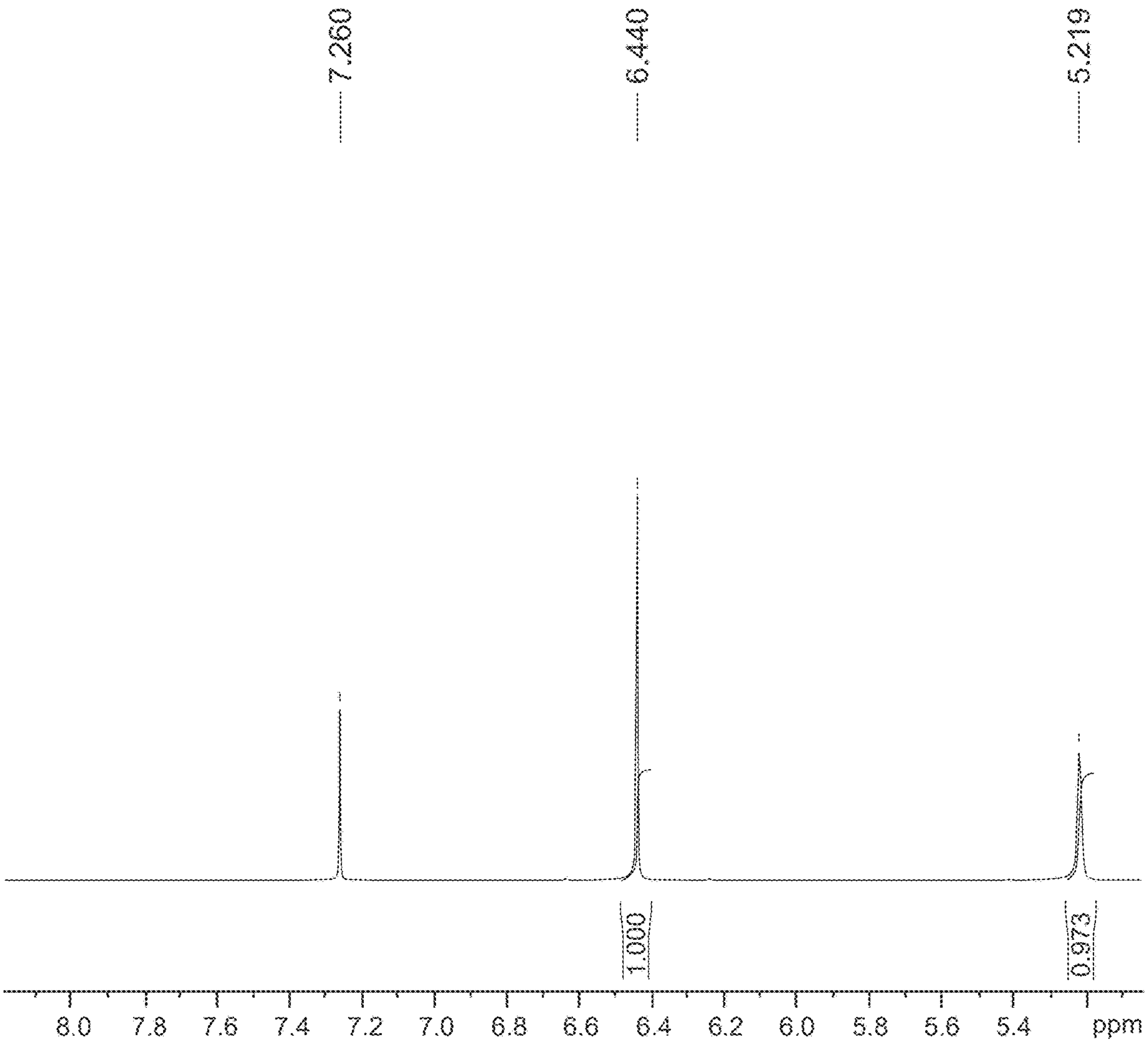

To a mixture of CBDA-ME (372 mg, 1 mmol) and potassium carbonate (330 mg, 2.5 mmol) in dimethylformamide (DMF) (5 mL) was added methyl iodide (0.5 mL) and stirred overnight under a nitrogen atmosphere at rt. Then water (20 mL) was added and the resulting mixture was extracted with ether. The organic layer was neutralized, dried over drying agent magnesium sulfate ($MgSO_4$) and then evaporated. The crude compound was then cleaned by column chromatography (3-5% ether-petroleum ether) to isolate the title compound (345 mg) as an oil. A copy of the NMR spectrum of EPM306 is shown in FIGS. 1A-F.

Example 4. In-Vivo Model of Pain

The therapeutic effect of EPM306 on pain is examined in the experimental model of hot-plate test, measuring the analgesic activity of EPM306 based on the reaction time of mice to lick their forepaws and/or jump after being placed on an aluminum hot plate heated to, and maintained at about 55° C. as described in the U.S. Pat. No. 5,338,753, with minor modifications. An aluminum surface is maintained at about 55° C. by circulating water through the passages in the metal. A clear plastic cylinder is placed on the surface to prevent escape. The end point is reached when the mouse either performed a hind paw lick or jumped off the surface; in no case are the animals kept more than 30 seconds on the plate. Control values are measured 3 hours before the test values. Mice are treated with EPM306 at different doses ninety (90) minutes before the hot plate test. The percent change in response time (latency) is calculated by comparing the mean of the control values with the mean of the test values and statistical significance determined by a paired t test.

Example 5. In-Vivo Model of Inflammatory

The therapeutic effect of EPM306 on inflammatory is examined in the experimental model of inflammation (paw edema) in arachidonic acid or platelet activating factor (PAF) injected mice, as described in the U.S. Pat. No. 5,338,753. Briefly, PAF (1.0 µg) or arachidonic acid (1.0 mg) dissolved in 50 µL of 5% ethanol in saline, is injected subcutaneously into the plantar surface of the right hind paw of ether-anesthetized CD-1 female mice (20-25 g). The volume of the right foot is measured to the level of the lateral malleous by water displacement before treatment, fifteen minutes after PAF injection, or thirty minutes after arachidonic acid injection. The mice are then treated with EPM306 injections at different doses. The change in paw volume is calculated for each mouse and the significance for each group is determined by a paired t test.

Example 6. In-Vivo, Pentylenetetrazole-Induced (PTZ) Model of Generalized Seizures The antiepileptic effects of EPM306 is tested in an acute experimental epilepsy model in pentylenetetrazole (PTZ) injected rats as described in Obay et. al. (Peptides, 2007, 28, 1214-1219). Briefly, adult male Wistar albino rats are divided into a control group, and four experimental groups with seven rats in each group. In order to generate epileptic seizures, PTZ (50 mg/kg) is injected intraperitoneally. The experimental groups receive intraperitoneal injections of EPM306 at different doses 30 min before PTZ injection. After PTZ injection, the rats are kept in cages and their behaviors are observed for 30 min. The latencies are separated into three components: first myoclonic jerk (FMJ), generalized clonic seizures (GCS) and tonic generalized extension (TGE).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A pharmaceutical composition comprising a therapeutically effective amount of a compound represented by the structure of Formula (Ia), and a pharmaceutically acceptable carrier or excipient, Formula (Ia)

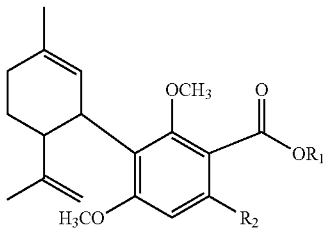

wherein $R_1$ is selected from the group consisting of a hydrogen, a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

$R_2$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl;

and stereoisomers, and salts thereof.

2. The pharmaceutical composition according to claim 1, which is represented by the structure of Formula (Ib), Formula (Ib)

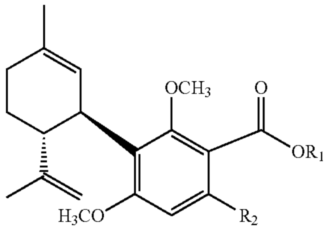

wherein $R_1$ and $R_2$ are defined as for Formula (Ia); and salts thereof.

3. The pharmaceutical composition according to claim 1, wherein $R_1$ is a linear unsubstituted $C_1$-$C_{15}$ alkyl.

4. The pharmaceutical composition according to claim 3, wherein $R_1$ is methyl.

5. The pharmaceutical composition according to claim 1, wherein $R_1$ is hydrogen.

6. The pharmaceutical composition according to claim 1, wherein $R_2$ is a linear unsubstituted $C_1$-$C_{15}$ alkyl.

7. The pharmaceutical composition according to claim 6, wherein $R_2$ is a linear unsubstituted $C_5$ alkyl.

8. The pharmaceutical composition according to claim 1, which is represented by the structure of Formula (IIIa), Formula (IIIa)

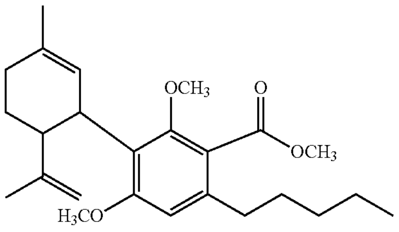

and stereoisomers thereof.

9. The pharmaceutical composition according to claim 1, which is represented by the structure of Formula (IIIb)

Formula (IIIb)

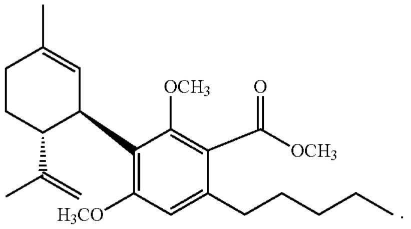

10. The pharmaceutical composition according to claim 1, which is represented by the structure of Formula (IIa), Formula (IIa)

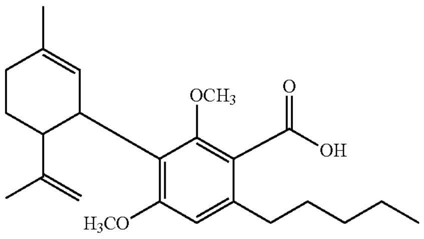

and stereoisomers, and salts thereof.

11. The pharmaceutical composition according to claim 1, which is represented by the structure of Formula (IIb), Formula (IIb)

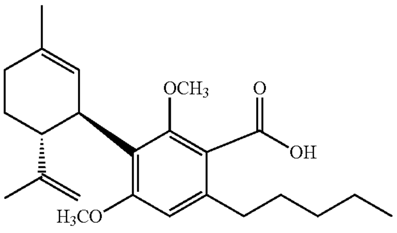

and salts thereof.

12. The pharmaceutical composition according to claim 1, wherein $R_1$ is selected from the group consisting of a linear or branched unsubstituted or substituted $C_1$-$C_{15}$ alkyl, a linear or branched unsubstituted or substituted $C_2$-$C_{15}$ alkenyl, and a linear or branched unsubstituted or substituted $C_2$-$C_{15}$ alkynyl.

* * * * *